(12) United States Patent
Batiste et al.

(10) Patent No.: US 8,684,960 B2
(45) Date of Patent: Apr. 1, 2014

(54) ENDOTHELIAL SCAFFOLD GRAFT AND METHOD THEREFOR

(76) Inventors: Stanley Batiste, Granite Bay, CA (US); Steven Achstein, Roseville, CA (US)

( * ) Notice: Subject to any disclaimer, the term of this patent is extended or adjusted under 35 U.S.C. 154(b) by 476 days.

(21) Appl. No.: 12/886,407

(22) Filed: Sep. 20, 2010

(65) Prior Publication Data

US 2011/0009947 A1 Jan. 13, 2011

Related U.S. Application Data

(63) Continuation-in-part of application No. 12/723,032, filed on Mar. 12, 2010.

(60) Provisional application No. 61/210,016, filed on Mar. 13, 2009.

(51) Int. Cl.
*A61M 5/00* (2006.01)
*A61F 2/06* (2013.01)
*A61F 2/04* (2013.01)

(52) U.S. Cl.
USPC ................... 604/8; 623/1.13; 600/36

(58) Field of Classification Search
USPC ............... 604/7–10, 99, 256; 128/24, 44, 64, 128/325–327, 673–677; 600/29–31, 36; 606/158; 251/8, 65; 623/1.1, 1.41, 623/1.42, 1.13
See application file for complete search history.

(56) References Cited

U.S. PATENT DOCUMENTS

| | | | |
|---|---|---|---|
| 3,826,257 A | 7/1974 | Buselmeier | |
| 4,549,879 A | 10/1985 | Groshong et al. | |
| 4,753,640 A | 6/1988 | Nichols et al. | |
| 5,713,859 A | 2/1998 | Finch, Jr. et al. | |
| 5,800,514 A | 9/1998 | Nunez et al. | |
| 5,849,036 A | 12/1998 | Zarate | |
| 6,056,717 A | 5/2000 | Finch et al. | |
| 6,146,414 A | 11/2000 | Gelman | |
| 6,338,724 B1 | 1/2002 | Dossa | |
| 6,371,981 B1 | 4/2002 | Yang et al. | |
| 6,461,321 B1 | 10/2002 | Quinn | |
| 6,585,762 B1 | 7/2003 | Stanish | |
| 6,598,278 B2 | 7/2003 | Chen et al. | |
| 7,025,741 B2 | 4/2006 | Cull | |
| 7,108,673 B1 | 9/2006 | Batiste | |
| 7,540,859 B2 | 6/2009 | Claude et al. | |
| 7,566,317 B1 | 7/2009 | Batiste et al. | |
| 2006/0229548 A1* | 10/2006 | Cull ................................ 604/7 |
| 2009/0234431 A1 | 9/2009 | Weinberger et al. | |

FOREIGN PATENT DOCUMENTS

WO    WO 2009/152488    6/2009

* cited by examiner

*Primary Examiner* — Philip R Wiest
(74) *Attorney, Agent, or Firm* — Weide & Miller, Ltd.

(57) ABSTRACT

An endothelial scaffold may used to form a graft with an endothelial lining or endothelium. The scaffold allows a natural vessel or other endothelial lumen to line a channel of the scaffold to provide an endothelial layer which enhances blood flow through the channel. The channel may have a narrowed section to provide a stenosis. One or more conduits may extend from an exterior portion of the scaffold to an inner surface of the channel. Air may be withdrawn from between the natural vessel and inner surface of the channel via the conduits to cause the endothelial lumen to conform to the inner surface of the channel. A valve may be used to prevent air from reentering the conduits. The graft, including the endothelial lumen, may be implanted into a patient.

14 Claims, 20 Drawing Sheets

ENDOTHELIAL SCAFFOLD GRAFT AND METHOD THEREFOR

CROSS-REFERENCE TO RELATED APPLICATION

This application is a continuation-in-part and claims priority to U.S. patent application Ser. No. 12/723,032 entitled Self Adjusting Venous Equalizing Graft, filed Mar. 12, 2010, which claims priority to U.S. Provisional Patent Application No. 61/210,016, filed Mar. 13, 2009.

BACKGROUND OF THE INVENTION

1. Field of the Invention

The invention relates generally to venous grafts and in particular to a self adjusting equalizing graft.

2. Related Art

There are currently more than 400,000 patients in the United States with end-stage renal disease (ESRD) and many times more than that throughout the world. ESRD accounts for approximately 6.4% of the overall Medicare budget at over $23 billion dollars in the US in 2006. Patients with end stage renal disease have lost their normal kidney function and as a result require dialysis to substitute the function of the kidney cleansing the blood. There are two types of dialysis; hemodialysis and peritoneal dialysis. For purposes of this overview we will primarily be focused on hemodialysis and later discuss briefly the topic of peritoneal dialysis.

Hemodialysis requires that large volume blood access and exchange be consistently available to sustain the life of the patient. Typically, a dialysis patient will require 3-4 hours of dialysis three days a week. The challenge with providing hemodialysis is maintaining access to large volumes of blood when a body constantly fights attempts to keep access available by healing closed such access. Currently there are three ways to provide hemodialysis; dialysis catheters, arterial venous fistulas (AVF's) and arterial venous grafts (AVGs). Although used world wide, catheters are known not to be efficient for long term dialysis. Unfortunately, catheters have very short patency rates and high rates of infection. For these reasons dialysis guidelines strongly oppose catheter use, other than short term, until fistula or graft placement is available.

AVG's and AVF's are synthetic and natural conduits respectively that are surgically placed to provide long term dialysis access. Both provide large diameter targets that can be easily accessed with large needles for blood exchange. These conduits are commonly placed in the arm with the furthest point attached to the patent's artery and then are directly attached to the vein for blood flow return. The high arterial blood pressure and flow is shunted directly to the vein providing dilatation of the vein or graft and large volume blood flow. Although these methods provide excellent means of access both have limitations with regard to sustaining long term patency. The patency rates are much greater than that of a catheter however overall are relatively poor when considering the few years gained in a patent's life. It has been noted that there is only 50% shunt patency at one year and less than 25% at 2 years. Not only does this create a huge burden on the cost of healthcare but more importantly, once access is no longer available, a new access point must be created to sustain a patient's life.

A thorough description of the reason for dialysis fistula and graft failure is beyond the scope of this document. The fundamental problem is that the flow dynamics created by these artificial conduits are not normal to our bodies. The change is detected by the body and the normal physiologic defenses become involved and attempt to return the system to normal.

From the discussion that follows, it will become apparent that the present invention addresses the deficiencies associated with the prior art while providing numerous additional advantages and benefits not contemplated or possible with prior art constructions.

SUMMARY OF THE INVENTION

An endothelial scaffold that forms a graft is disclosed herein. The graft formed with the scaffold may utilize a harvested natural vessel or other channel or lumen having an endothelium to form a lining which enhances blood flow through the graft by preventing clotting, among other things. In other words, the graft may have an endothelial lining or endothelium comprising one or more endothelial cells to enhance blood flow through the graft. The graft may have a narrowed portion to provide a stenosis.

The graft may be configured in a variety of ways. For example, in one exemplary embodiment, an endothelial scaffold graft comprises a scaffold having a channel (configured to accept an endothelial lumen) therethrough, a protrusion configured to narrow a portion of the channel extending from an interior surface of the channel, and one or more conduits extending to an interior surface of the channel. The protrusion may be centrally located along the length of the channel.

The conduits may have at least one external access point on the scaffold. In addition, the conduits may extend to a location on the interior surface of the channel that is adjacent the protrusion. A one way valve may be connected to the conduits and configured to allow gas to be withdrawn from the conduits while preventing gas from entering the conduits.

A first opening may be in the scaffold at a first end of the channel and a second opening may be in the scaffold at a second end of the channel. The first opening may be configured to allow a first portion of the endothelial lumen to be folded over the scaffold and the second opening may be configured to allow a second portion of the endothelial lumen to be folded over the scaffold. The first opening, second opening, or both may taper inward to reduce the width of the scaffold at the first opening The graft may include an endothelial lumen comprising a harvested vessel that has an endothelial coating comprising one or more endothelial cells. The endothelial lumen may extend from a first end to a second end of the channel to form a lining of the channel. A drug eluting material configured to release one or more cellular growth inhibitors may be on the interior surface of the channel.

In another exemplary embodiment, the graft may comprise a scaffold having a first end and a second end, one or more conduits extending from an exterior surface of the scaffold to an inner surface of the channel, a valve in fluid communication with the conduits configured to prevent gas from entering the conduits while permitting gas to be withdrawn from the conduits, and a protrusion extending from an inner surface of the channel. The scaffold may be configured to form a channel to accept an endothelial lumen. The scaffold may have a reduced thickness at the first end configured to allow the endothelial lumen to be rolled over the scaffold at the first end. The conduits may extend to a location on the interior surface of the channel that is adjacent the protrusion.

The channel may comprise a first opening at the first end and a second opening at the second end. The protrusion may be configured to narrow a portion of the channel to provide a stenosis in the channel. The graft may also comprise an endothelial lumen comprising a vessel harvested from a person.

Such a harvested vessel may comprise an endothelial coating comprising one or more endothelial cells. The endothelial lumen may extend from the first end to the second end of the channel to form a lining of the channel. A drug eluting material configured to release one or more cellular growth inhibitors may be on the interior surface of the channel.

One or more grooves may be on the exterior surface of the scaffold. The grooves may be configured to engage one or more fixation bands to secure the endothelial lumen in place. One or more protruding portions may be on the exterior surface of the scaffold. The protruding portions may be located adjacent the grooves.

Various methods of forming an endothelial scaffold graft are disclosed herein. For example, in one embodiment, a method comprises providing a scaffold having a channel configured to accept an endothelial lumen therethrough, providing a protrusion configured to narrow a portion of the channel extending from an interior surface of the channel, and providing one or more channels extending to the interior surface of the opening. The channels may have at least one external access point on an exterior surface of the scaffold.

A drug eluting material configured to release one or more cellular growth inhibitors may be provided on the interior surface of the opening. A thickness of the scaffold at an end of the scaffold may be reduced to allow an end of the endothelial lumen to be rolled over the end of the scaffold. A vein may be inserted into the opening such that the vein extends from a first end of the opening to a second end of the opening. It is noted that the vein may be harvested from a patient's vascular system, such as by cutting a section of vein from the vascular system.

Air between the vein and the interior surface of the opening may be removed by removing the air via the one or more channels. In addition, the method may include rolling an end of the vein over one end of the scaffold, and placing a fixation band around the endothelial scaffold at the groove to secure the end of the vein in position.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE PREFERRED EMBODIMENTS

Figure 1:
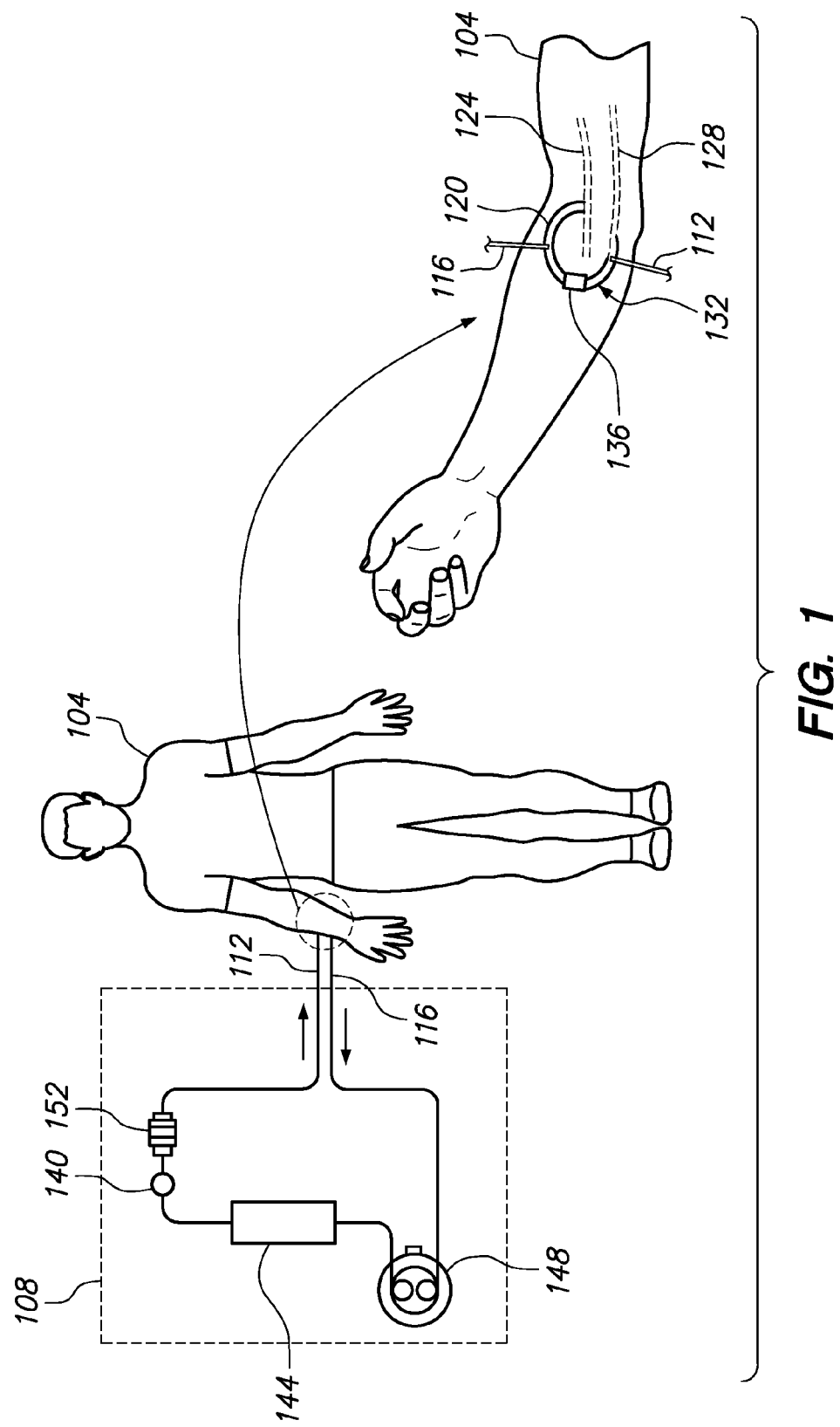
FIG. 1 illustrates a dialysis machine connected to a patient and placement of an exemplary self-adjusting graft according to an embodiment of the invention.

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The self adjusting venous equalizing graft (SAVE graft) disclosed herein provides a self regulating stenosis. The stenosis creates a higher pressure blood flow at one end of the graft and a lower pressure flow at the other end of the graft. This provides the benefit of a lower pressure where blood flows from the graft to the vein, while still maintaining a higher pressure on the arterial side of the stenosis and at a point where blood may be drawn to a dialysis machine. The lower pressure more closely matches the natural pressure of the circulatory system while the higher pressure allows blood to be efficiently drawn to a dialysis machine and to serve circulatory needs downstream the artery from the graft. It will be understood that though generally described herein with regard to dialysis and dialysis machines, the SAVE graft may benefit and be used with other circulatory procedures.

The configuration of a stenosis may range from abrupt to smooth tapering or any other shape to create the restriction. Also, a stenosis is generally positioned between both access points or sides of a graft. It is contemplated that the stenosis may be located at any point between the intake and outtake opening. This design maintains high pressure on the arterial end (proximal end) which is the end of the graft for drawing off the patient's blood by the dialysis machine. It is contemplated that the stenosis may be located at any point between the intake and outtake opening.

One advantage of this stenosis is that it creates resistance to blood flow which lowers the pressure of the blood returning from the dialysis machine to the patient. The low pressure nature of the returning flow blood eases the pressure on a patient's vein(s) from blood returning from a dialysis machine. This damping of the pressure and flow rate creates a system like that of normal physiology when the patient is not subject to having a graft. This is important as it has been shown that most grafts fail due to the increased pressure and flow at the point in which the graft connects to a vein. Failure may occur due to a type of intraluminal scarring (intimal hyperplasia) within the veins, slowly closing the veins off at or near the point of graft outflow.

Another advantage is that the SAVE graft's stenosis reduces or eliminates the "stealing" of blood by a dialysis machine or the like. To illustrate, traditionally, patients have had a continuous high flow/high pressure shunt or graft implanted for dialysis. This type of shunt may cause blood flow to bypass or be reduced to portions of the patient's circulatory system. In this manner, the shunt creates what is called in medicine a "steal", which steals blood from the heart by bypassing the body's tissues and returning blood to the heart unused. This creates undue and continued stress on the heart and can cause a situation where the blood flow to the hand, arm, or other extremities is compromised. In fact, most dialysis related access conflicts arise from grafts which steal blood from the hand, decreasing circulation/perfusion and resulting in loss of fingers.

Traditional grafts may be configured with a fixed stenosis or an operator adjustable stenosis. For example, a stenosis balloon design may be used to provide the stenosis described above in an adjustable manner. The balloon may inflate or deflate to adjust and maintain the stenosis, and hence blood pressure, within a graft. This design generally comprises four main components: a dialysis graft, a central stenosis balloon, an injection port, and a catheter connecting the reservoir to the balloon. These components may be placed surgically and, except for the external control portions, may remain under a patient's skin for the life of the graft. However, the stenosis must be adjusted by a physician or a trained operator. Even then, it is difficult for a physician to determine the best pressure, and because blood pressure is not static, this selected pressure may be non-ideal over the course of a day as the patient is active or sleeping.

In contrast to a fixed stenosis and the operator or physician adjustable stenosis, the SAVE graft uses a stenosis that is self regulating. The self regulating stenosis allows the pressure from the inflow, outflow, or both ends of a graft to adjust the stenosis allowing for optimal venous outflow pressures and flow rates. By using this method there will be no operator error in stenosis adjustment and there will be advantages achieved with improved graft hemodynamics.

The SAVE graft may be configured in various ways that use the graft's internal pressure regulating ability to create the optimum flow dynamics for hemodialysis. Some configurations and details of use are described in detail below. It will become apparent to one skilled in the art from the descriptions herein that elements of the various configurations herein may be combined in different embodiments of the SAVE graft.

FIG. 1 illustrates a patient 104 undergoing dialysis. As shown, a dialysis machine 108 is connected to the patient's forearm by an inflow tube 116 and an outflow tube 112. The exemplary dialysis machine 108 comprises a pump 148, a dialyzer 144, a pressure monitor 140, and an air trap 152 to perform its function. It will be understood that other dialysis machines or other blood processing devices may be used with the SAVE graft. A patient's blood may enter the dialysis machine 108 from the inflow tube 116. Once processed by the dialysis machine 108, the blood may return to the patient 104 via the outflow tube 112.

As shown in FIG. 1, an arterial venous graft (AVG) 120 having a SAVE graft 136 may be located in a patient's 104 forearm or upper arm, or any other location in the body. It is contemplated that the SAVE graft 136 may be utilized as a stand alone graft, or with dialysis, or any other access in intervention procedure. This configuration allows inflow and outflow tubes 116, 112 to be connected to the patient's forearm or upper arm. The proximal end of the AVG 120 may be attached to an artery 124 and the distal end may be attached to a vein 128. The pressure differential between the artery 124 and the vein 128 dictates that flow travels thought the AVG 120 from the proximal (i.e. arterial) end towards the distal (i.e. venous) end. For this reason, the inflow tube 116 of a dialysis machine 108 may be connected to the arterial end of the AVG 120 while the outflow tube is connected to the venous end of the AVG.

Figure 2A:
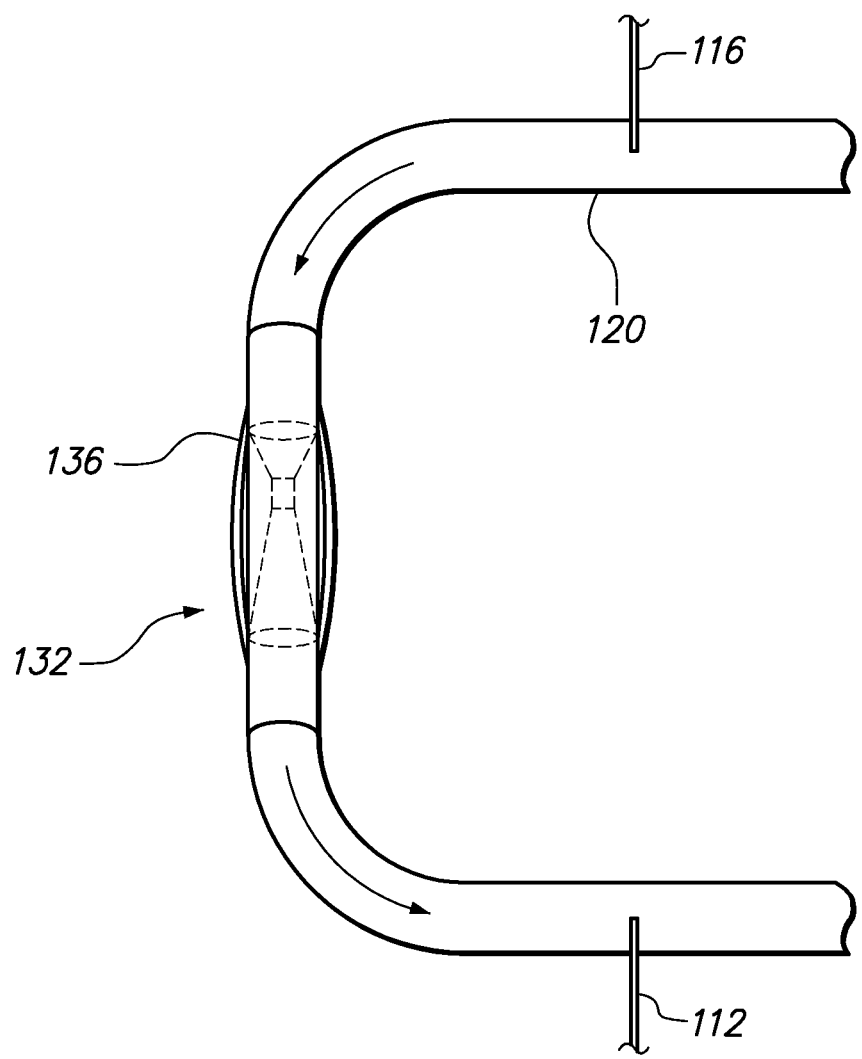
FIG. 2A is a cross section view illustrating an exemplary self-adjusting graft in place.

The SAVE graft 136 may be positioned at the apex 132 of the AVG 120 to create resistance to blood flow within the AVG, such as by providing a central stenosis. This ultimately decreases the pressure and return flow to the vein 128. FIG. 2A provides a better view of an exemplary SAVE graft 136 within an AVG 120. As shown, the SAVE graft 136 is positioned generally at the apex of the AVG 120. Of course, it is contemplated that the SAVE graft 136 may be positioned at any locations along or within an AVG 120.

FIG. 2A also illustrates how inflow and outflow conduits may access a patient's blood flow with respect to the SAVE graft 136. As shown, the blood flow, illustrated by the arrows of FIG. 2A, is flowing from a proximal (i.e. arterial) end of the SAVE graft 136 towards the distal (i.e. venous) end of the SAVE graft. Access to the blood flow by an inflow tube 116 may be at the arterial end where blood pressure is higher while return of the blood flow by an outflow tube 112 may be at the venous end where pressure is lower to achieve the benefits discussed herein.

Access to the patient's blood flow by the inflow tube 116, outflow tube 112, or both may be through the AVG 120, such as illustrated, or through the SAVE graft 136 itself. For example, the inflow tube 116, outflow tube 112, or both may access blood flow through a portion of the SAVE graft 136. It is contemplated that the inflow tube 116 may access blood flow at the arterial end of the SAVE graft 136 directly through a patient's artery. Likewise, the outflow tube 116 may return blood directly to a patient's vein at the venous end of the SAVE graft 136.

The SAVE graft 136 may be attached to the AVG 120 or other graft in various ways. For example, the ends of a SAVE graft 136 may be bonded, adhered, and/or fused to the AVG 120 such that a fluid pathway extends through the SAVE graft and the portions of the AVG attached to the SAVE graft.

Figure 2B:
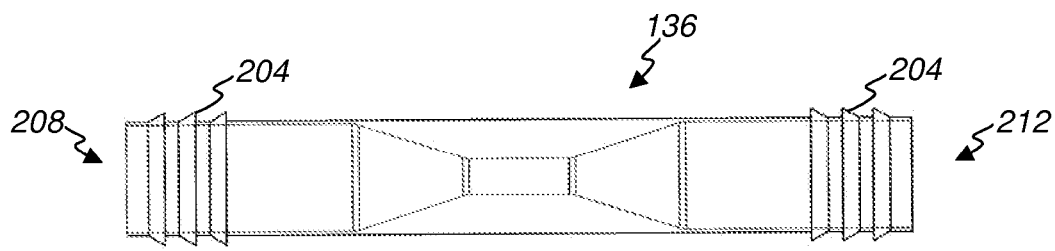
FIG. 2B a cross section view illustrating an exemplary self-adjusting graft having attachment ends.
Figure 2C:
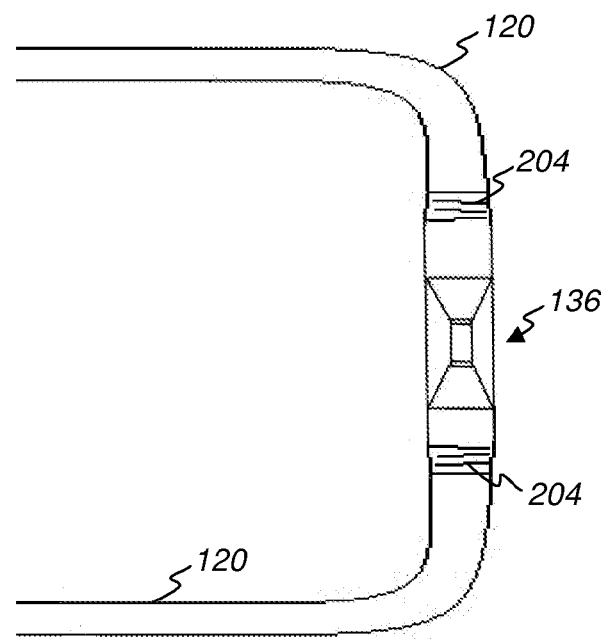
FIG. 2C is a cross section view illustrating an exemplary self-adjusting graft in place.

The SAVE graft 136 may comprise one or more elements configured to facilitate attachment to an AVG 120. For example, as shown in FIG. 2B, the SAVE graft 136 has ends 208,212 configured for attachment to an AVG 120 or other graft. As shown, the SAVE graft 136 comprises ridges 204 at its ends 208,212 which may engage the interior of an AVG 120. One or more ridges 204 may be at either or both ends 208,212 of the SAVE graft 136. The SAVE graft 136 may attach to the AVG 120 such as shown in FIG. 2C. As can be seen in FIG. 2C, a fluid pathway from a first section of the AVG 120 to the SAVE graft 136 and through a second section of the AVG may be formed by such attachment.

Referring back to FIG. 2B, the ridges 204 may extend outward from an exterior surface of the SAVE graft 136. The AVG 120 may conform to the ridges 204 after insertion to secure the SAVE graft 136 in position. The ridges 204 may be angled so as to allow the ends 208,212 of the SAVE graft 136 to be inserted into an AVG to form the connection to the other graft. The angled ridges 204 may also resist removal of the ends 208,212 from an AVG. For example, as shown, the ridges 204 are angled so as to present a lower profile when the SAVE graft 136 is being inserted and a larger profile if the SAVE graft were to be moved in the opposite direction.

Though shown as generally perpendicular to the SAVE graft 136, the ridges 204 may be at various orientations. For example, it is contemplated that the ridges 204 may be angled or in a spiral configuration such as to allow the SAVE graft 136 to be threaded or "screwed" into an AVG.

In one or more embodiments, the SAVE graft may have an internal conduit which allows blood to flow through the SAVE graft. The internal conduit may have one or more expandable portions and one or more collapsible portions, as will be described further below. In one or more embodiments, the space or area between the internal conduit and the outer wall of the SAVE graft may form a pressure reservoir. Expansion of the expandable portion into the pressure reservoir causes an increase in pressure within the reservoir. The increased pressure causes the collapsible portion to narrow or collapse thereby narrowing the stenosis of the SAVE graft. As pressure is decreased within the pressure reservoir, the collapsible portion may return to an uncollapsed state widening the stenosis of the SAVE graft.

Figure 3:
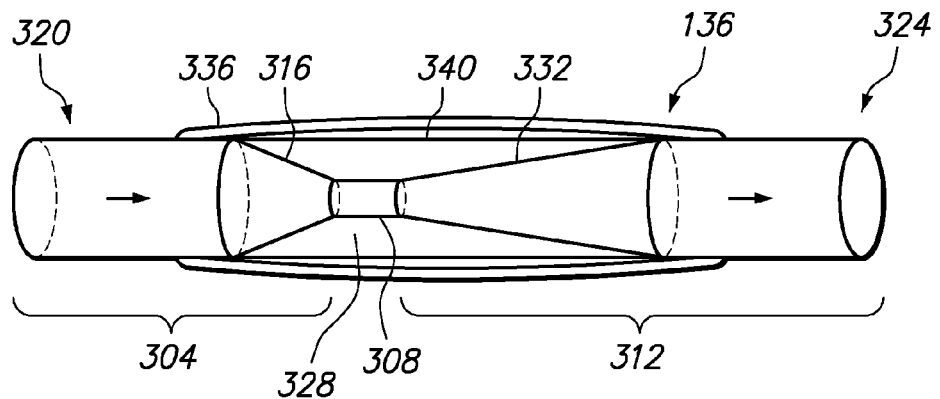
FIG. 3 is a cross section view illustrating an exemplary self-adjusting graft.

As shown in FIG. 3, the SAVE graft may comprise an internal conduit between an inflow end 320 and an outflow end 324 of the graft which forms a fluid pathway for blood flow through the graft. For example, as shown the internal conduit comprises an arterial pressure control surface (APCS) 316, a stenosis control diaphragm (SCD) 308, and a venous pressure control surface (VPCS) 332. An outer wall 340 may extend the length of the SAVE graft 136 and support various parts of the SAVE graft therein, as described further below. In one embodiment, the ends of the outer wall 340 form an inflow end 320 and an outflow end 324 for blood flow as shown by the arrows of FIG. 3. The outer wall 340 or a portion thereof may be surrounded by a puncture prevention guard (PPG) 336 which protects the SAVE graft 136 from damage, among other things, as will be described further below.

The arterial portion 304, SCD 308, and venous portion 312 will generally be in fluid communication such as shown in FIG. 3. The arterial portion 304 accepts blood flow at an inflow end 320 of the SAVE graft 136. The arterial portion 304 may comprise an arterial pressure control surface 316 which tapers toward the SCD 308. As shown for example, the APCS 316 is tapered conical portion of the arterial portion 304. The APCS 316 may be formed from resilient flexible or stretchable material. The compliance of this material may thus act as a plane to direct force to a pressure reservoir 328, which will be described further below. It is noted that the APCS 316 may also be formed from an inflexible or substantially inflexible material to direct force to the pressure reservoir 328 in one or more embodiments.

The venous portion 312 allows blood to flow out of the SAVE graft 136 at an outflow end 324. The direction of blood flow within the venous portion 312 is illustrated by the arrow therein. The venous portion 312 may comprise a venous pressure control surface 332. In one or more embodiments, the VPCS 332 may be constructed with a smooth conical tapering surface directed away from the SCD 308. The VPCS 332 may also be formed from resilient flexible or stretchable material to allow the VPCS to deform or expand with changes in blood pressure within the venous end 312 of the SAVE graft 136. When venous pressures increases, the deformation or expansion of the VPCS 332 creates increased pressure within the pressure reservoir 328. In this manner, the VPCS 332 forms an expandable portion of the SAVE graft's internal conduit.

In one or more embodiments, the pressure reservoir 328 may be a reservoir formed between the internal conduit and the outer wall 340 of the SAVE graft. For instance, as shown the pressure reservoir 328 may be formed around the APCS 316, the SCD 308, and the VPCS 332 as shown in FIG. 3. As pressure within the pressure reservoir 328 increases, such as caused by the expansion of the VPCS 332 due to increased venous pressure, the SCD 308 (or collapsible portion of the SAVE graft's internal conduit) may be deformed inward or collapse as will be described below. Typically, but not always, the pressure reservoir 328 may be filled with material of low compressibility. The filler transfers force from the expansion of the VPCS 332, the APCS 316, or both to the SCD 308, deforming the SCD inward. It is contemplated that the filler material may be liquid or gaseous in one or more embodiments.

Figure 4A:
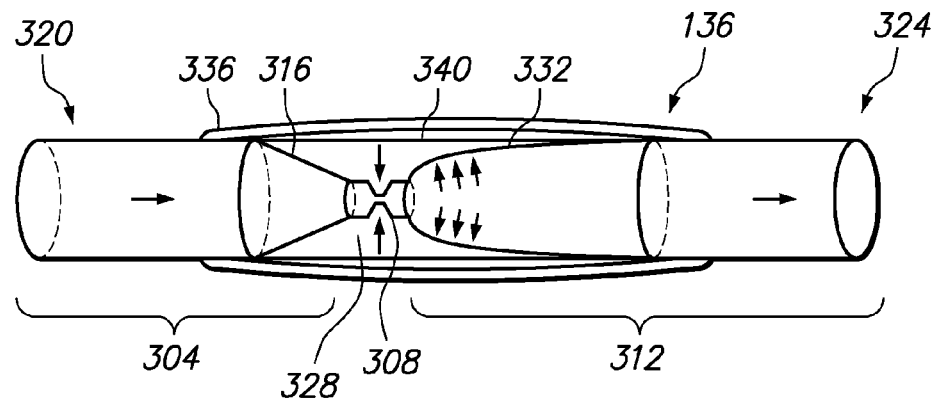
FIG. 4A is a cross section view illustrating an exemplary self-adjusting graft in an increased pressure state.

FIG. 4A illustrates a SAVE graft in an increased or high venous pressure state. In this state, blood pressure at the outflow end 324 of the SAVE graft is increased or high. As can be seen by the arrows of FIG. 4A, the pressure has caused the VPCS 332 to expand increasing pressure within the pressure reservoir 328. The increased pressure within the pressure reservoir 328 acts upon the SCD 308 deforming it inward, as illustrated by the inward arrows of FIG. 4A. This inward deformity will lead to a circumferential dilatation of the SCD 308 which will narrow the inner lumen of the SAVE graft. This narrows the stenosis provided by the SAVE graft. The narrowed stenosis increases the resistance to blood flow through the arterial and venous ends which decreases the flow rate. The decreased flow rate leads to decreased venous volume and therefore decreased venous pressures.

Figure 4B:
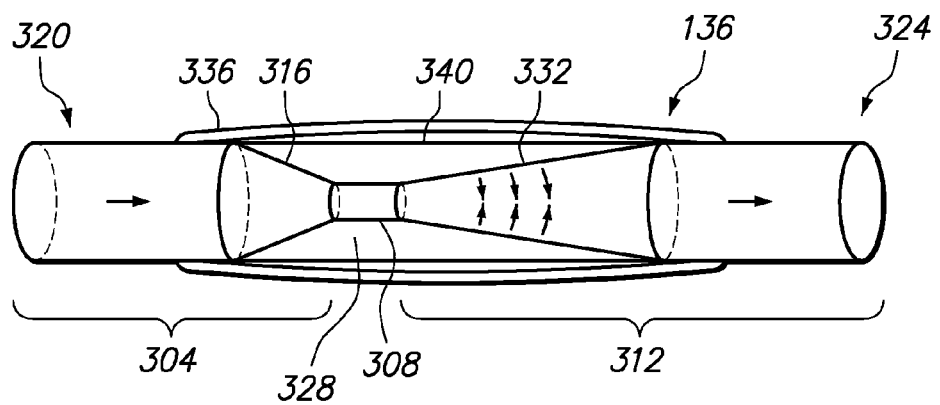
FIG. 4B is a cross section view illustrating an exemplary self-adjusting graft in a decreased pressure state.

Conversely, as shown in FIG. 4B, as venous pressures decrease, the pressure inside the pressure reservoir 328 will decrease and the SCD 308 will expand outward increasing the luminal diameter of the SAVE graft 136, thus increasing flow through the graft. In turn, pressure at the outflow is increased.

The SCD 308 may be formed from various resilient flexible materials to allow the SCD to collapse or narrow and also return to a substantially or fully uncollapsed state. For example, the SCD 308 may be formed from rubber, plastic, or both. The walls SCD 308 may have thinner sections in one or more embodiments to allow the SCD to better respond to pressure changes within the pressure reservoir 328. In addition, or alternatively, the materials used to form the SCD 308 may be selected for their flexibility. In this manner, the SCD 308 may deform inward the desired amount for a given pressure within the pressure reservoir 328.

It is noted that the VPCS 332, the APCS 316, the SCD 308, or all three may have a different flexibilities, such as by being formed from different materials or various thicknesses, than the SCD 308 in one or more embodiments. In this manner, the SAVE graft's 136 sensitivity to pressure at the arterial end 320, the venous end 324, or both may be configured. For example, in one embodiment, the VPCS 332 may be formed from highly flexible material making the SAVE graft 136 more sensitive to venous pressure. In some embodiments, the APCS 316 may be formed from relatively rigid material to make the SAVE graft 136 less sensitive to arterial pressure.

As shown in FIG. 3, the SAVE graft 136 has a tapered or conical shaped APCS 316 and VPCS 332. This shape is beneficial as it provides a smooth slope towards the narrower SCD 308 in which blood may flow. In addition, the tapered shape helps direct pressure within the pressure reservoir 328 to the SCD 308 causing the SCD to collapse when appropriate. Of course, other shapes may be used. For example, the APCS 316, VPCS 332, or both may be square, rounded, rectangular, or other shapes.

Also as shown, the VPCS 332 has a larger volume than the APCS 316. This is beneficial in that it allows the VPCS 332 to exert more pressure on the pressure reservoir 328. In this manner, the SAVE graft 136 may be configured to be more sensitive to venous pressure. It is contemplated that the VPCS 332, APCS 316, or both may have different sizes. For example, they may be substantially equal in size, or the APCS 316 may be larger than the VPCS 332. This allows the SAVE graft 136 to be configured for various blood pressures allowing the graft to be used at various locations in a patient's body.

It is noted that the APCS 316 and VPCS 332 may be the same length in one or more embodiments, or have different lengths. Different lengths allow the SAVE graft 136 to respond differently to changes in arterial and venous pressure. For this reason, it is also contemplated that the SCD 308 may be longer than the APCS 316 and VPCS 332 in one or more embodiments.

As can be seen from the above, the SAVE graft 136 provides self regulation of blood pressure on both sides of the graft. The material and design dimensions of the SAVE graft 136 reduce the venous outflow to physiologic or natural levels while maintaining the required arterial pressure.

In some embodiments, an outer housing unit or puncture prevention guard (PPG) 336 may be included. The PPG 336 provides various benefits. The PPG 336 may be used to prevent the dialysis staff or other individual or event from inversely puncturing the inner components of the SAVE graft 136. The PPG 336 may also act as a reinforcing covering to prevent pressurization of the pressure reservoir 328 from expanding the outer wall 340 of the SAVE graft.

In some embodiments, the PPG 336 may be configured to allow outward expansion of the pressure reservoir 328, such as for the purpose of allowing a balloon angioplasty to be performed. As can be seen, the space between the PPG 336 and the outer wall 340 of the graft allows for expansion of the pressure reservoir 328. To illustrate, if the SAVE graft 136 were to stop flowing, clot intervention would be needed to clear the graft. Intervention of this type often requires balloon angioplasty. If needed, the SAVE graft 336 may be constructed so that a balloon can be fully expanded within the graft. When dilated with a balloon, the outer wall 340 will expand into the space provided by the PPG thus sparing the graft from damage.

As stated above, the SAVE graft 136 may be configured differently in various embodiments. For example, the internal conduit of a SAVE graft 136 need not form a pressure reservoir in all embodiments. It is contemplated that the collapsible portion of the internal conduit may contract (i.e., collapse) and expand from blood pressure of a surrounding blood flow as will be described below.

Figure 5A:
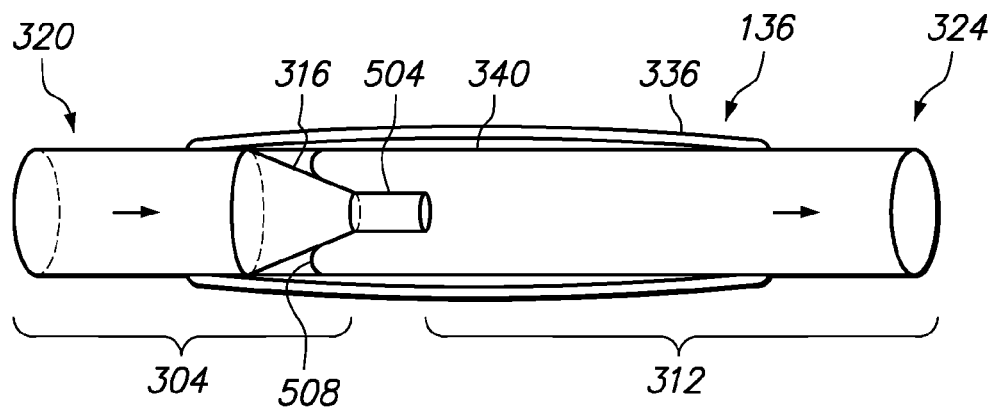
FIG. 5A is a cross section view illustrating an exemplary self-adjusting graft.

To illustrate, as shown in the embodiment of FIG. 5A, the SAVE graft 136 may have an open venous portion 312. In this embodiment, the VPCS and pressure reservoir may not be required and thus may not be included as part of the SAVE graft 136. This creates an open configuration that allows the venous pressure to act directly upon a venous controlled pressure nozzle (VCPN) 504 determining the luminal diameter and thus self regulating the stenosis provided by the SAVE graft 136. As will be described further below, the direct action of the venous pressure on the VCPN 504 allows the stenosis provided by the VCPN to be self regulated without the use of a pressure reservoir. Like the above embodiments, in this embodiment, the inflow end 320 may accept blood flow from an artery while the outflow end 324 allows blood to return to a patient through a vein.

Like the SCD of the above embodiments, a VCPN 504 may be a collapsible portion of the SAVE graft's internal conduit in one or more embodiments. The VCPN 504 may be formed from resilient flexible material such as described above with regard to other flexible or stretchable parts of the SAVE graft 136. In one embodiment, the VCPN 504 is cylindrical in shape. Of course other shapes may be used. For example, the VCPN 504 may be rectangular or square, include a taper, or be a combination thereof. A taper may be beneficial in that a taper may be more responsive to changes in pressure than a non-tapered shape.

Figure 5B:
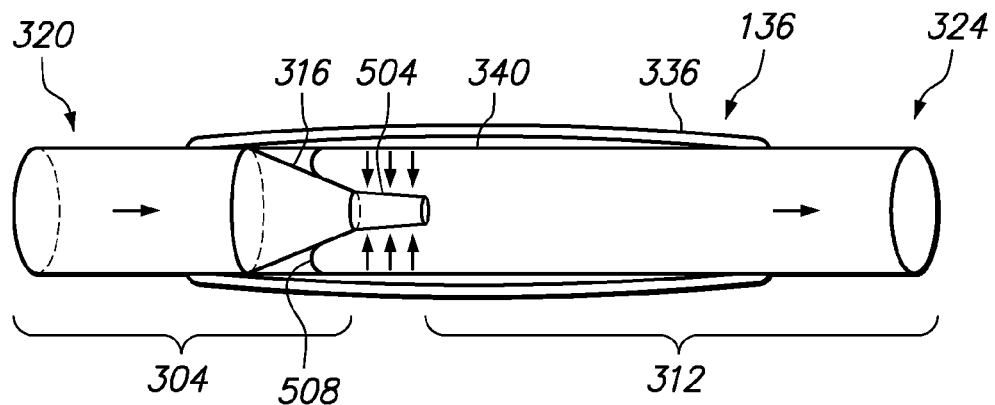
FIG. 5B is a cross section view illustrating an exemplary self-adjusting graft in an increased pressure state.

As shown by the arrows in FIG. 5B, during times of increased or high venous pressure the forces exerted by the pressure acts directly on a VCPN 504 to narrow the inner luminal diameter of the SAVE graft 136 thus restricting blood flow. At low venous pressure the VCPN 504 expands which expands the inner luminal diameter and allows increased blood flow. This is possible with a compliant VCPN 504 which expands or contracts based on the forces exerted by venous pressure.

In open configurations, clot prevention barriers 508 may be provided to prevent blood from pooling and clotting within the SAVE graft 136. In one or more embodiments, clot prevention barriers 508 prevent clotting by not allowing blood to reaching crevices or other areas within a SAVE graft 136 where the blood may become stagnant or pool. For example, a clot prevention barrier 508 may have a rounded shape to encourage blood flow to prevent pooling and clotting.

It is noted that in the above embodiments having a VPCS 332 (such as illustrated in FIG. 3), blood is channeled through the VPCS avoiding most if not all clot prone crevices or areas within a SAVE graft. In an open configuration, such as that of FIGS. 5A and 5B, it can be seen that without clot prevention barriers 508, blood may reach clot prone areas such as the area between the APCS 316 and the outer wall 304 of the SAVE graft. For this reason, clot prevention barriers 508 are advantageous in SAVE grafts 136 having an open configuration. Of course, clot prevention barriers 508 may also benefit other configurations of SAVE grafts 136 where there are areas prone to clotting.

To illustrate, in FIG. 5A, a clot prevention barrier 508 prevents blood from reaching an angled crevice between the outer wall 304 and the APCS 316 where it may clot. It is contemplated that one or more clot prevention barriers 508 may be used in other locations or embodiments of a SAVE graft as well. For example, in embodiments with a VPCS, a clot prevention barrier may be located around the VPCS to prevent blood from reaching a crevice formed between the VPCS and the outer wall of a SAVE graft (as can be seen in FIG. 3). Of course, clot prevention barriers 508 may not be required where there is little of no risk of clotting. It is noted that the materials used to form a clot prevention barrier 508 or other element of a SAVE graft 136 may include one or more anticoagulants to reduce the risk of clotting.

As can be seen, the SAVE graft provides a stenosis which is self regulating. As stated above, this is advantageous in that the stenosis does not have to be adjusted by an operator or physician. In this way, the SAVE graft is not susceptible to operator error the way other stenosis grafts are. The self regulating stenosis also self regulates for changes in a patient's blood pressure even if these changes are for a short period of time. A fixed stenosis does not provide this capability. In addition, an operator adjusted stenosis can only adjust through an operator's actions. Thus, small changes in blood pressure or changes in blood pressure which are not of sufficient duration to be detected by an operator may not be adjusted for.

The self regulated stenosis created by a SAVE graft provides the desired hemodynamic effects needed to improve dialysis and prevent many of the major problems associated with dialysis. For instance, a SAVE graft decreases the recirculation rates (non-dialyzed blood mixing with dialyzed blood) improving dialysis efficiency.

In addition, the SAVE graft allows normalization of the venous outflow pressures. Normally veins are low pressure systems. In a patient with a dialysis graft the large conduit attached to the artery transports blood with high flow and pressures into the graft and out though the patient's native veins. The native veins however cannot accommodate this high flow and pressure and eventually scar and shut down which is typically known as graft failure. The stenosis within the SAVE graft causes resistance to dampen this flow and pressure. In this manner, the stenosis creates an environment which is natural to the patient's circulatory system.

The SAVE graft also provides increased proximal arterial pressures. As stated above, the stenosis provided by the SAVE graft maintains the pressure at the arterial end preventing a steal syndrome which takes blood from the artery which can lead to limb loss or damage.

Another benefit of a SAVE graft is a reduction in loss of cardiac output. The resistance created by the stenosis of the SAVE graft creates resistance to flow which decreases loss of cardiac output. With the dialysis grafts and fistulas, high pressure and flow continuously course through the graft. Blood flow from the heart goes through the graft and then returns back to the lungs and heart without perfusing any tissue. This wastes the heart motion and puts excess strain on the heart through the patient's life.

Figure 6A:
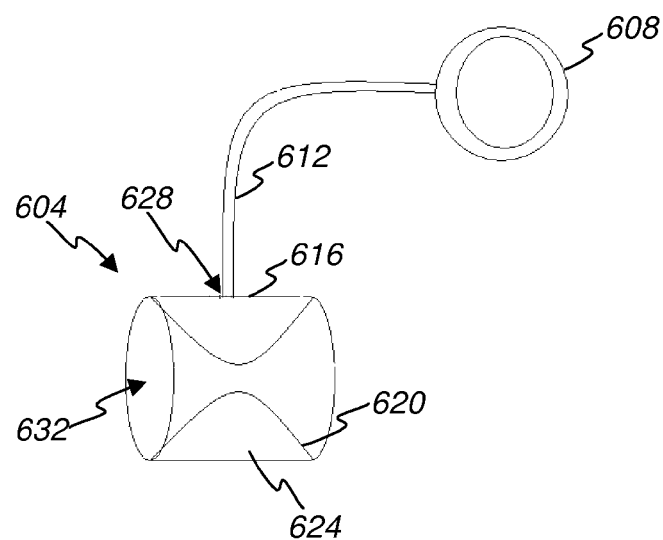
FIG. 6A is a side view illustrating an exemplary stenosis attachment.

Having described benefits of providing a stenosis above with regard to the SAVE graft, it is also contemplated herein that a stenosis may be provided in various other ways. For instance, FIG. 6A illustrates a stenosis attachment 604 which may be placed around an AVG or other graft to allow such graft to provide a stenosis. In other words, the stenosis attachment 604 may be used to retrofit existing grafts so that they may provide a stenosis.

In one or more embodiments, the stenosis attachment 604 may comprise a tubular structure having an inner wall 620 and an outer wall 616. The tubular shape provides a channel 632 to accept an AVG or other graft. The outer wall 620 and inner wall 616 may have a circular cross sectional shape, such as shown in FIG. 6A, to allow the stenosis attachment 604 to accept at least a portion of a cylindrical AVG or other graft, as will be described further below. Of course other cross sectional shapes may be used.

The outer wall 620 and inner wall 616 may be sealed to one another to form a reservoir 624 between the outer wall and inner wall. In the embodiment shown for example, the outer wall 620 and inner wall 616 are sealed together at their edges. The seal may be formed in various ways, now known or later developed. For example, the seal may be formed by one or more adhesives, welds, crimps, or a combination thereof. Of course, a seal may also be formed when the outer wall 620 and inner wall 616 are integrally formed.

Typically, the reservoir 624 will be configured to retain a filler material, such as a fluid or a gas, without allowing such material to leak from the reservoir. In this manner, the reservoir 624 may be "inflated" or expand as it is filled with the filler material. Generally, the reservoir 624 will be configured to expand inward to create a stenosis. This may be accomplished in various ways.

In one embodiment, the inner wall 620 may be formed from flexible and/or expandable material. This material may also be resilient to allow it to recover its shape. The outer wall 616 may be formed from a more rigid material. In this manner, as the reservoir 624 is inflated with filler material, the flexible inner wall 620 may expand inward while the outer wall 616 generally retains its shape. As can be seen in FIG. 6A, the inner wall 620 expands inward as the reservoir 624 is filled with filler material. This inward expansion narrows the channel 632.

An injection port 608 may be provided to inflate and deflate (i.e. fill and empty) the reservoir 624 in one or more embodiments. This allows the amount of stenosis provided by the stenosis attachment to be controlled. For this reason, it is contemplated that the injection port 608 may be external to a patient's body in one or more embodiments. The injection port 608 may also be implanted in a patient's body, such as below the skin surface to be readily accessible.

The injection port 608 may be configured to move filler material to the reservoir 624 to inflate the reservoir. In one embodiment for example, a syringe may be used to introduce fluid or other material into the injection port. This causes the inner wall 620 to expand inward which narrowing a stenosis provided by the stenosis attachment 604. In addition, the injection port 608 may also remove or release filler material from the reservoir 624 to deflate the reservoir. For example, in one embodiment, a syringe may be used to withdraw material from the injection port. This causes the inner wall 620 to return to an un-expanded state thereby decreasing the narrowing provided by the stenosis attachment 604. It is noted that the resiliency of the inner wall 620 allows the inner wall and thus the reservoir 624 to automatically return to an un-expanded state when the filler material is removed or released from the reservoir.

As can be seen, the injection port 608 may be connected to the reservoir 624 by a conduit 612 which allows filler material to flow between the injection port and the reservoir. The conduit 612 may be a tubular structure with a first end attached to the injection port 608 and a second end attached to the reservoir 624 to allow this flow of filler material. The conduit 612 may attach to an opening 628 in the outer wall 616 of the stenosis attachment 604 to allow filler material to flow into and out of the reservoir via the conduit.

The injection port 608 may function in various ways. For example, the injection port 608 may comprise a pump which pumps filler material from into the reservoir 624 through the conduit 612. The injection port 608, conduit 612, or both may include a release valve which prevents filler material from escaping the reservoir 624 unless deflation of the reservoir is desired. When activated, the release valve may allow filler material to flow out of the opening 628 and back towards the injection port 608. It is contemplated that the filler material may be stored in the injection port 608 so that it may be later used to fill the reservoir 624 again.

Figure 6B:
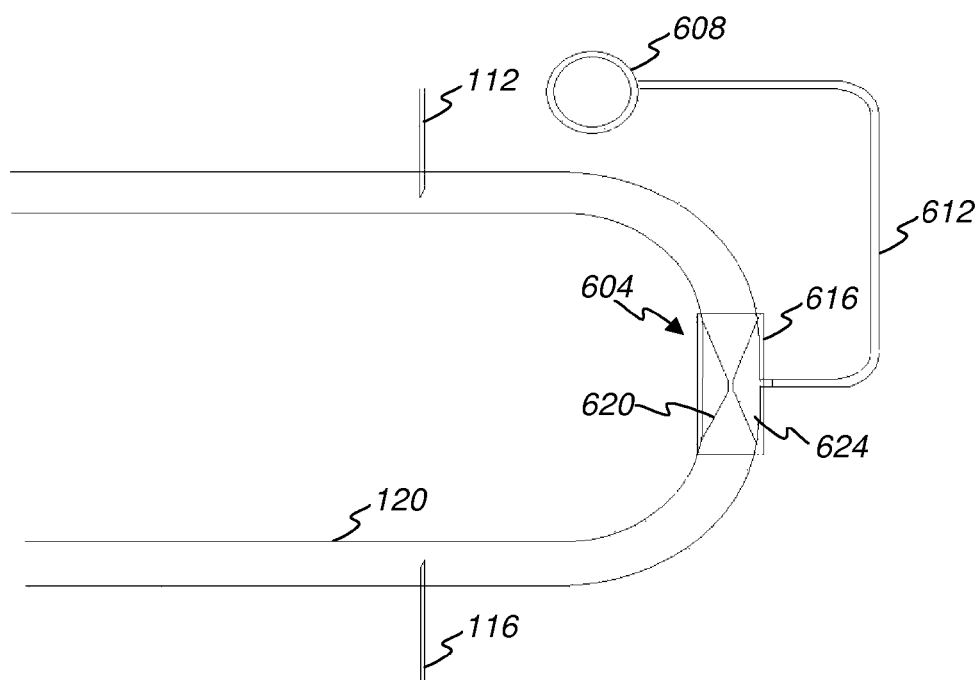
FIG. 6B is a side view illustrating an exemplary stenosis attachment on a graft.

FIG. 6B illustrates a stenosis attachment 604 placed on an AVG graft 120. Like the SAVE graft, the stenosis attachment 604 may be placed at the apex of the graft 120, or at other locations along the graft. In addition, the stenosis attachment 604 may be used with various types of grafts where a stenosis would be beneficial. For example, the stenosis attachment 604 may provide a stenosis for an AVG graft 120 or other graft used to provide access to blood flow for dialysis (or other procedures) via an inflow tube 116 and an outflow tube 112. As can be seen, the stenosis attachment 604 provides a stenosis for the graft 120 which ordinarily would not provide a stenosis. In this manner, a standard AVG graft 120 or other graft may be enhanced with the benefits of a stenosis.

The injection port 608 may be operated to inflate or deflate the reservoir 624 of the stenosis attachment 604. This causes the inner wall 620 of the stenosis attachment 604 to expand inward which presses on and constricts the AVG graft 120. As can be seen, the force of the inner wall 620 narrows the AVG graft 120 narrowing its diameter where the inner wall contacts the AVG graft. This provides a stenosis through the AVG graft 120. Deflating the reservoir 624 causes the inner wall 620 to return towards the outer wall 616 and allows the AVG graft 120 to expand to its normal diameter as well. It will be understood that the reservoir 624 may be inflated various amounts to control or adjust the stenosis or narrowing provided by the stenosis attachment 604 and AVG graft 120.

It is contemplated that a doctor or other personnel may measure one or more blood flow characteristics, such as flow rate, oxygenation, and/or pressure. After adjusting a stenosis, the doctor may verify that the desired blood flow characteristics have been created through such adjustment. For example, the doctor may measure flow rate, oxygenation, and/or pressure at a point within or outside the stenosis attachment 604. If the desired characteristic or characteristics are present, the adjustment procedure may be completed, such as by fixing the current amount of filler material in the reservoir. For example, the opening through which filler material enters and exits the reservoir may be sealed or closed to keep the amount of stenosis fixed.

The stenosis attachment 604 may be installed on an AVG graft 120 or other graft before or after the graft is implanted in a patient. Generally, this occurs by inserting the AVG graft 120 through the opening 632 of the stenosis attachment 604 such as shown in FIG. 6A. The stenosis attachment 604 may be slid or moved along the AVG graft 120 to a desired position. As shown in FIG. 6B for example, the stenosis attachment 604 has been moved to the apex of the AVG graft 120.

Where the AVG graft 120 is already in a patient, the stenosis attachment 604 may be installed by disconnecting one end of the graft to allow the end of the graft to be inserted into the opening of the stenosis attachment. The stenosis attachment 604 may then be positioned along the AVG graft 120 as desired. The disconnected end of the AVG graft 120 may then reattach to an artery or vein to allow blood flow to resume through the graft.

Figure 7A:
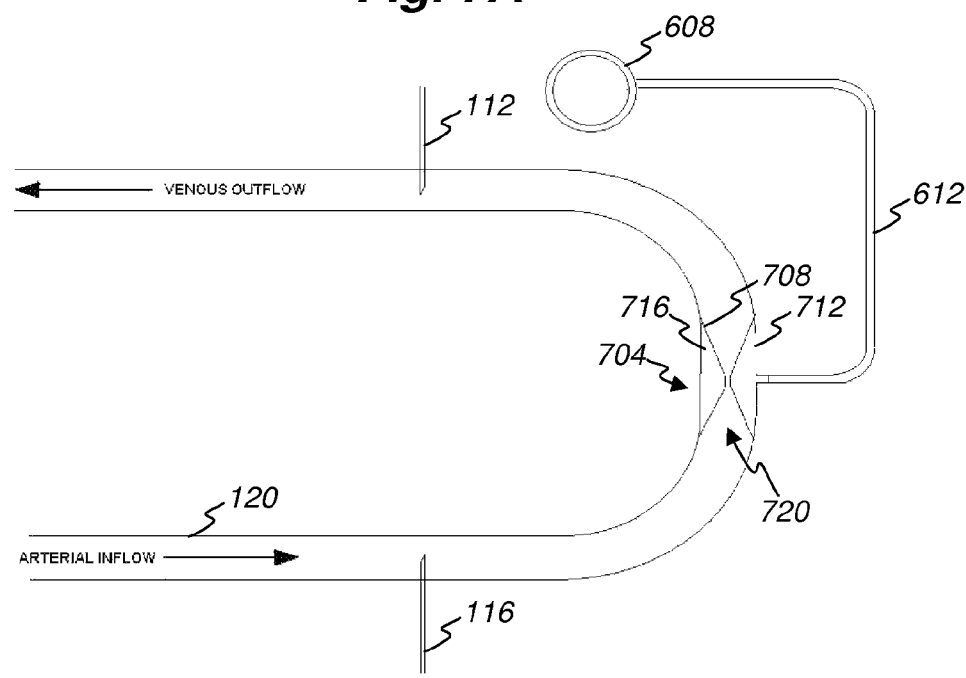
FIG. 7A is a side view illustrating an exemplary adjustable stenosis in a graft.

It is contemplated that an adjustable stenosis may be directly provided by a graft having an expanding or contracting inner wall. For example, FIG. 7A illustrates an adjustable stenosis 704 that is part of a graft 120. Like the SAVE graft, the adjustable stenosis 704 may be placed at the apex of the graft 120, or at other locations along the graft. In addition, the adjustable stenosis 704 may be used with various types of grafts where a stenosis would be beneficial. For example, the adjustable stenosis 704 may be used with a graft that provides access to blood flow for dialysis (or other procedures) via an inflow tube 116 and an outflow tube 112.

The adjustable stenosis 704 may comprise a resilient inner wall 708 and an outer wall 712 which form a tubular shape having an channel 720 therethrough to allow blood to flow through the adjustable stenosis. The inner wall 708 and outer wall 712 may form a reservoir 716 within the adjustable stenosis 704. For example, similar to above, the inner wall 708 and 712 may be attached at the edges to form a reservoir 716. An opening in the outer wall 712 may be provided to connect the reservoir 716 to an external pressure controlling device or devices. For example, the reservoir 716 may be connected at the opening to an injection port 608 by a conduit 612. Manipulating the pressure within the reservoir 716 causes the expansion and contraction of the reservoir to adjust the stenosis provided, as will now be described with regard to FIGS. 7B-7E.

Figure 7B:
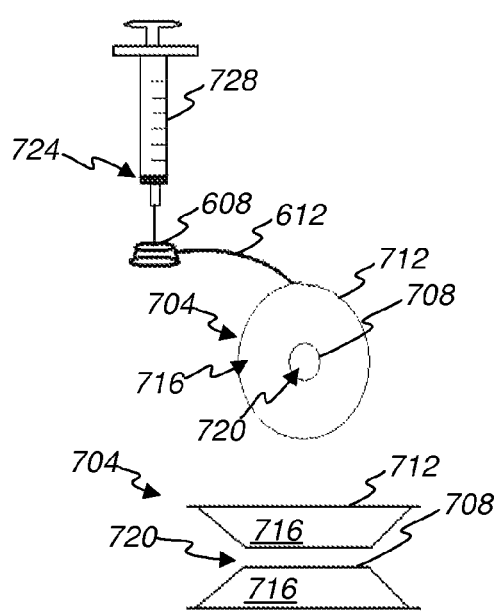
FIG. 7B is a side and cross section view illustrating an exemplary adjustable stenosis in a neutral position.

FIGS. 7B-7E illustrate a side view above a cross section view of the adjustable stenosis 704 to show the change in stenosis, among other things. In one or more embodiments, the reservoir 716 may be formed in an expanded shape such as shown in FIG. 7B. For instance, the inner wall 708 may be curved, bent, or otherwise shaped to give the reservoir 716 an expanded shape where the inner wall 708 is positioned a distance away from the outer wall. In this state, the pressure of filler material within the reservoir 716 may be similar or the same as the pressure outside the reservoir.

As the filler material 724 is evacuated from the reservoir 716 the pressure outside the reservoir becomes greater than the internal pressure. As can be seen in FIGS. 7B-7E for example, as filler material 724 is withdrawn from the reservoir 716 and into the syringe 728, external pressure increases relative to pressure within the reservoir 716 causing the reservoir to contract and reduce the amount of stenosis 720. Filler material 724 may be withdraw from the reservoir 716 via an opening in the outer wall. The opening may be sealed to prevent filler material from reentering the reservoir 716. For example, the injection port 608 may self-seal once the syringe needle is removed. This prevents filler material from expanding the reservoir 716.

The process may be reversed to expand the reservoir 716. For example, reintroducing the filler material 724 balances the internal and external pressure eventually returning the reservoir 716 to its original expanded state. Since the inner wall 708 may be formed to have an expanded shape, it is contemplated that once the seal is removed the inner wall will automatically return to its expanded shape. Alternatively, filler material may be injected into the reservoir 716 to return the reservoir to its expanded shape.

Figure 7C:
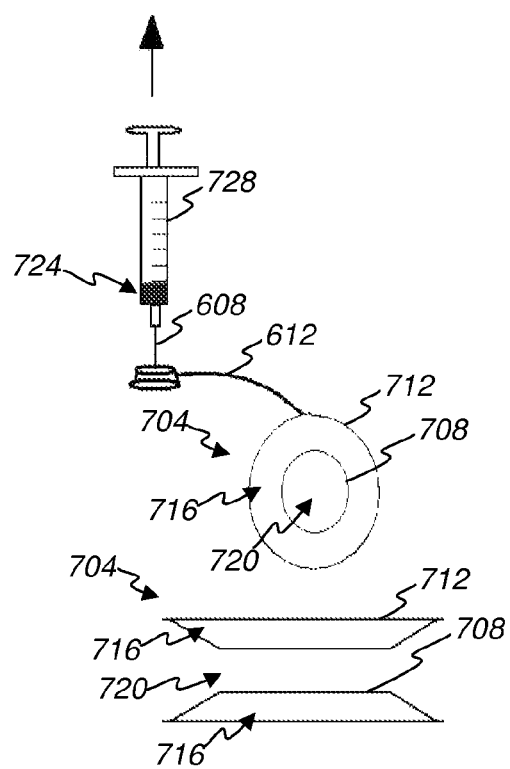
FIG. 7C is a side and cross section view illustrating an exemplary adjustable stenosis in an aspirated position.
Figure 7D:
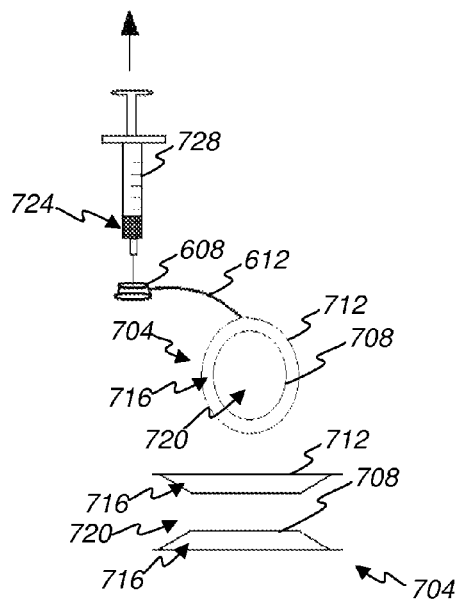
FIG. 7D is a side and cross section view illustrating an exemplary adjustable stenosis in a further aspirated position.
Figure 7E:
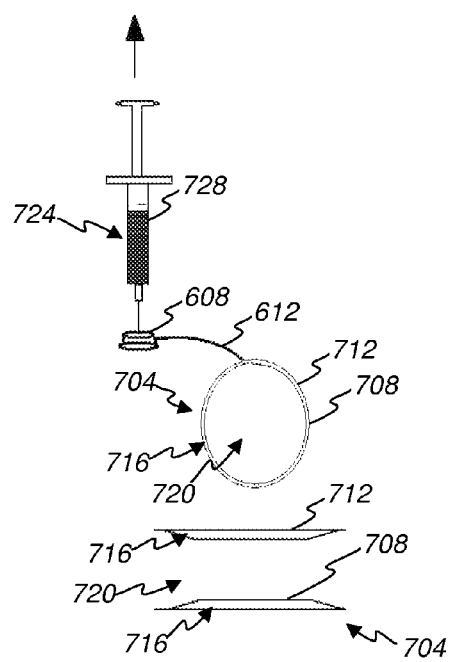
FIG. 7E is a side and cross section view illustrating an exemplary adjustable stenosis in a completely aspirated position.

As FIGS. 7C and 7D illustrate, this allows the stenosis 720 to be adjusted to a desired amount anywhere between a fully collapsed state and a fully expanded state. By adjusting the amount of filler material within the reservoir 716. It is contemplated that the reservoir 716 (e.g., the inner wall 708 of the reservoir) may be formed from a resilient stretchable material which reduces or eliminates wrinkling or creasing, in one or more embodiments.

The reservoir 716 may have a variety of configurations. For example, FIGS. 7F-7I illustrate a reservoir 716 having a plurality of segments or chambers. In one or more embodiments, the chambers may be in fluid communication so as to allow filler material to enter and exit the chambers. For example, a conduit may connect the chambers in one or more embodiments. In this manner, the chambers may be inflated or deflated at the same time.

The chambers may be formed by connecting or attaching portions of the inner wall 708 to the outer wall 712 such as shown. It is contemplated that the chamber forming connections may be perforated or have one or more openings to form the conduits that put the chambers to be in fluid communication. The inner wall 708 may be formed from resilient or elastic material capable of stretching. In this manner, as filler material 724 is moved into or out of the reservoir 716, the chambers may expand or contract to adjust the provided stenosis.

It is noted that the reservoir 716 may be configured to have a "default" expanded or contracted state. For example, in the embodiments described with regarding to FIGS. 7B-7E, the reservoir 716 is configured to have a expanded shape. Thus, the reservoir 716 defaults to its expanded shape unless the pressure therein is being manipulated. For instance, the reservoir 716 of these embodiments default to an expanded shape unless filler material is withdrawn to reduce the pressure within the reservoir relative to external pressure.

In the embodiments described with regard to FIGS. 7F-7I, the reservoir 716 and its chambers are configured in a contracted state and expand when filler material is injected. Since the reservoir 716 and its chambers are shaped in a contracted state, the reservoir and its chambers default to a contracted state unless the pressure therein is being manipulated. For instance, the reservoir 716 and its chambers remain contracted unless filler material is injected to pressurize (and thus expand) the reservoir/chambers. It is contemplated that a reservoir 716 with or without chambers may be configured to have a default expanded or contracted state.

FIGS. 7F-7I which illustrate a side view and cross section view of an adjustable stenosis 704 having a default contracted state. As can be seen, as filler material 724 is moved from the syringe 728 to the chambers, the chambers expand increasing the stenosis 720. In this embodiment, the filler material 724 may pressurize the interior of the chambers causing them to expand. The process may be reversed by moving filler material 724 out of the reservoir's chambers. As pressure within the chambers is reduced, the chambers contract decreasing the stenosis 720.

Figure 7F:
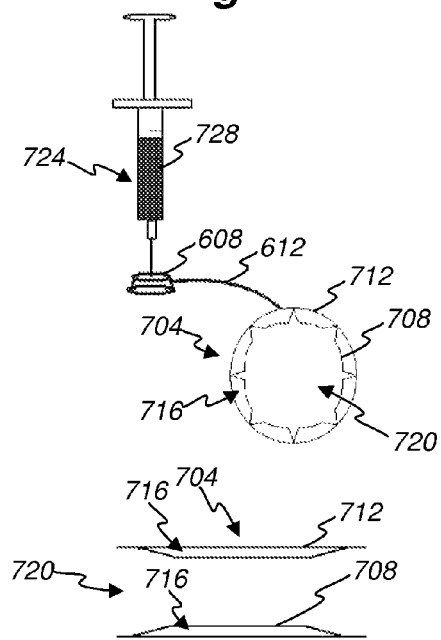
FIG. 7F is a side and cross section view illustrating an exemplary adjustable stenosis in a neutral position.
Figure 7G:
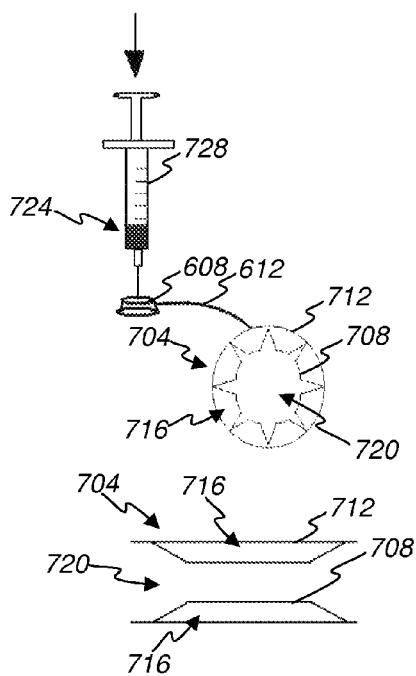
FIG. 7G is a side and cross section view illustrating an exemplary adjustable stenosis in an aspirated position.
Figure 7H:
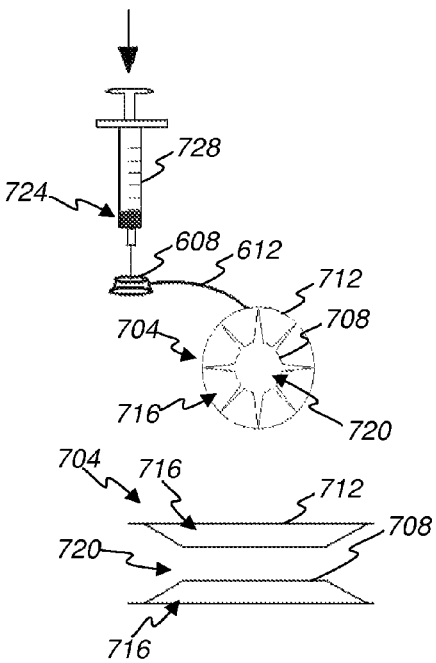
FIG. 7H is a side and cross section view illustrating an exemplary adjustable stenosis in a further aspirated position.
Figure 7I:
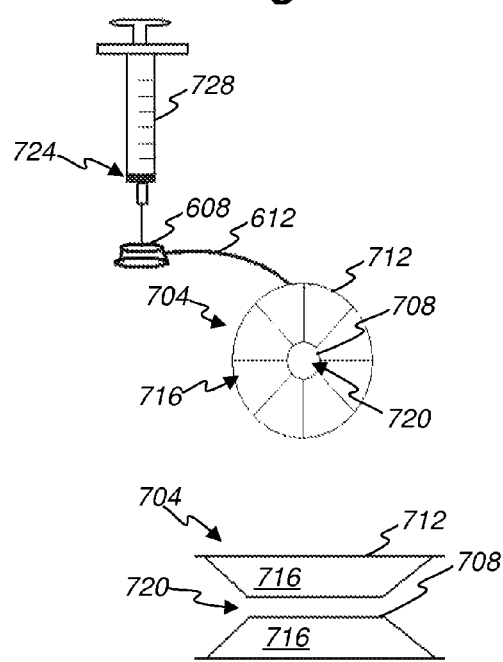
FIG. 7I is a side and cross section view illustrating an exemplary adjustable stenosis in a completely aspirated position.

In one or more embodiments, the chambers may be formed from a resilient or stretchable material. The chambers may be configured such that they expand to form corresponding shapes or structures which may meet as they are inflated, such as shown in FIG. 7I. This design is advantageous in that the amount of possible creasing and wrinkling is reduced or eliminated as the chambers are inflated or pressurized. In one embodiment, the chambers may have a reduced profile prior to being inflated, such as shown in FIG. 7F. As filler material is moved into the chambers the chambers may expand into the channel 720, as shown in FIGS. 7G-7I.

As described above with regard to the stenosis attachment, a doctor or other personnel may make one or more measurements to determine the amount of stenosis required to achieve a particular blood flow characteristic. Likewise, with the adjustable stenosis the amount of filler material within a reservoir may be varied to achieve a desired blood flow characteristic or characteristics. Once adjusted, the doctor may verify that the desired blood flow characteristic(s) are present. If verified, the current amount of stenosis may be fixed such as by fixing the amount of filler material presently in the adjustable stenosis' reservoir. For example, an opening used to inject or withdraw filter material into the reservoir may be sealed or closed to keep the amount of stenosis at its current level.

The initial incorporation of a graft or conduit, such as a SAVE graft or an AVG graft, takes place when a thin layer of tissue called fibrin forms on the inner wall of a graft. Fibrin coats all foreign bodies which enter the body. Then, a patient's endothelial cells which line all other arteries/veins then grow in throughout the graft. The endothelium is the thin layer of endothelial cells that line the interior surface of the vascular system. In fact, endothelial cells line the entire circulatory system, from the heart to the smallest capillary. These cells reduce turbulence in the flow of blood allowing the blood to be pumped farther.

Recently, it has been shown that endothelium can grow in a laboratory environment. Patient specific endothelial cells may be harvested from a patient's own vascular system. These cells may then be cultured and can be grown on surfaces and independently as sheets of cells. Currently, the objective of such culturing of cells is for use in future vessel repair. In addition to the above, what is herein contemplated and disclosed is an improved graft apparatus and method utilizing a patient's endothelial cells.

The endothelium normally provides a non-thrombogenic surface because it contains heparin which acts as a cofactor for activating antithrombin III, a protease that cleaves several factors in the coagulation cascade. The improved dialysis graft incorporates this non-thrombogenic property to increase graft patency. Such increase is highly advantageous in terms of patent health and comfort. To illustrate, it has been noted that there is only 50% graft patency at one year and less than 25% after two years in the case of AVGs placed for long term dialysis access. This creates a large burden on healthcare costs and, more importantly, once access is no longer available, a patient's life may no longer be sustainable.

There are multiple designs of dialysis grafts from the single hollow tube designs to designs having pre-made, adjustable or fixed stenosis at the ends of the graft. In addition, unique designs exist, such as those with fixed or adjustable stenosis in the middle of the graft to provide optimal flow characteristics for graft longevity. These designs may include fixed stenosis, adjustable stenosis, and self adjusting stenosis which auto-regulates flow throughout the graft. The unique designs are made to provide resistance centrally within the graft so that the exiting flow is of decreased pressure, flow rate and has less pulsation.

The improved dialysis graft may employ various graft designs, such as those described above, and include the unique properties to improve graft patency. As will be described further below, the improved dialysis graft described herein may include one or more of the following: covering a fixed, central stenosis within the graft with endothelium as described above; utilizing a drug eluting material as described below which inhibits cellular and fibrin growth within a graft; and harvesting a patient's vein(s) as the source of endothelial covering.

Figure 8A:
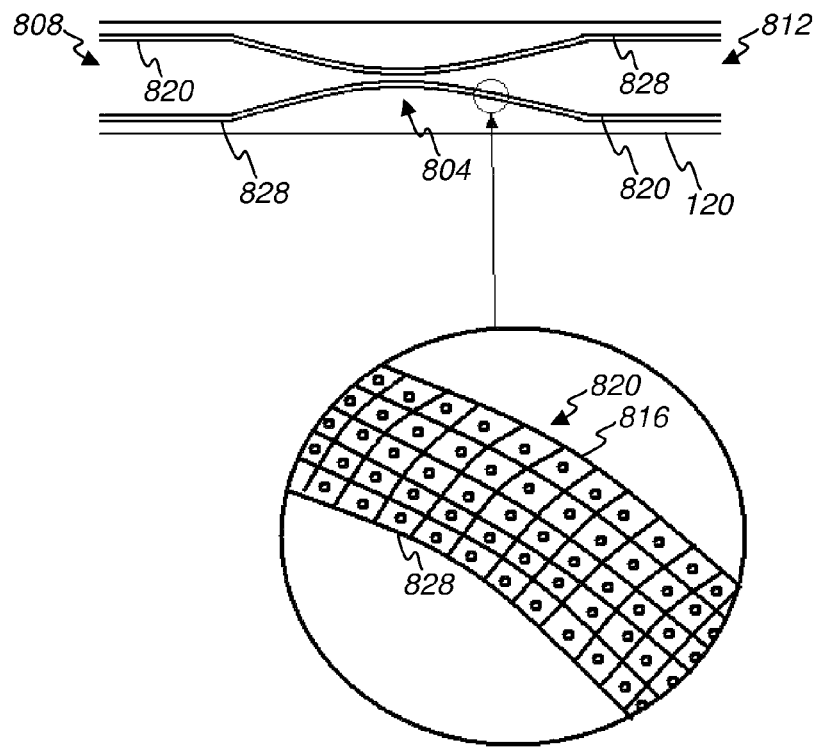
FIG. 8A is a cross section view illustrating an exemplary improved vascular graft having an endothelial lining.
Figure 8B:
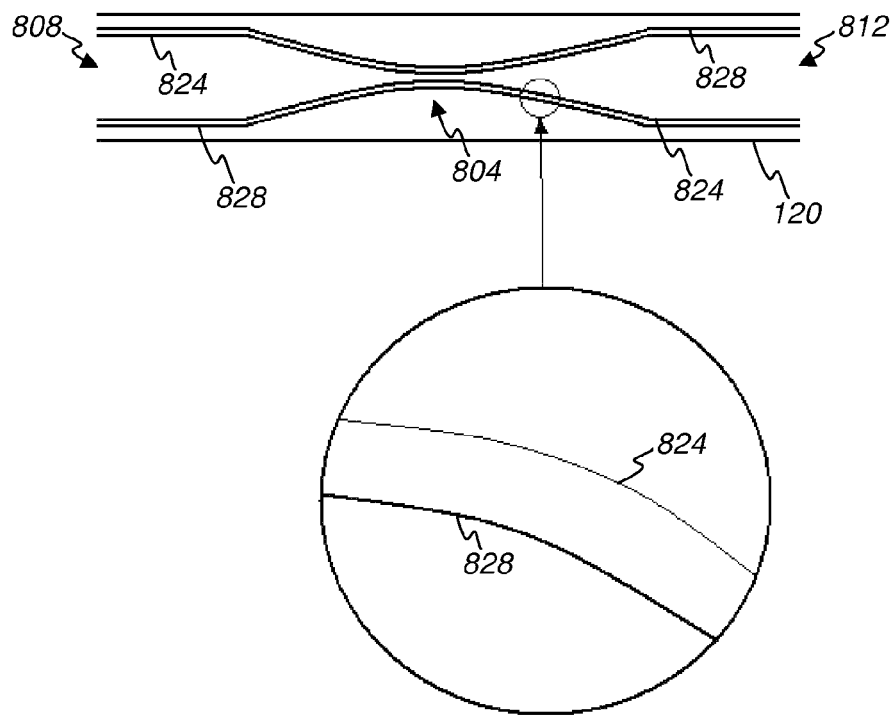
FIG. 8B is a cross section view illustrating an exemplary improved vascular graft having a drug eluting material.

As shown in FIGS. 8A-8B, a central stenosis may be coated or covered with endothelial cells (such as those grown in a laboratory), drug eluting materials, or both. As mentioned above, the endothelial coating may be used to prevent blood from clotting which improves graft patency, and the drug eluting material may be used to stop cellular proliferation.

In FIG. 8A, an exemplary AVG 120 having an endothelial coating 820 on the surface of its fluid pathway from a first end 808 to a second end 812 of the AVG is illustrated. The AVG 120 provides a central stenosis 804 which is also coated or lined with the endothelial coating 820. The endothelial coating 820 may comprise endothelial cells 816 grown in a laboratory, harvested from a patient, or both. As can be seen, the endothelial coating 820 provides a surface which contacts blood as it flows through the graft. This allows the endothelial coating 820 to prevent clotting thus improving graft patency.

FIG. 8B illustrates an exemplary AVG 120 having a drug eluting coating 824 on the surface of its fluid pathway between a first end 808 and a second end 812 of the AVG 120. This AVG 120 also includes a central stenosis 804. The central stenosis 804 may be coated or lined with the drug eluting coating 824 such as shown in FIG. 8B. In this manner, the drug eluting coating 824 may release compounds that interact with blood as it flows through the AVG 120. This allows the drug eluting coating 824 to stop unwanted cellular proliferation, such as the proliferation of fibrin cells.

The drug eluting coating 824 may comprise various materials. Typically, the drug eluting coating 824 comprises a polymer that holds and elutes (releases) a drug or other compound at the graft wall. The drug eluting coating 824 may be a durable coating or may be designed to biodegrade after or as the drug is eluted. The drug eluting coating 824 may be spray coated or dip coated. In addition, there may be one, two, three, or more layers in the coating. These layers may be the same material such as to provide a thicker coating or may be different materials used for their different properties (e.g., a base layer may be used for adhesion, a main layer for holding the drug, and a top coat to control the release of the drug and extend its effect).

As stated above, the drug or compound released may be configured mainly to inhibit neointimal growth (due to proliferation of smooth muscle cells) which would cause restenosis. Much of the neointimal hyperplasia seems to be caused by inflammation. Thus, immunosuppressive and antiproliferative compounds may be present in the drug eluting coating 824. Example drugs that may be used include sirolimus and paclitaxel, though it is contemplated that the drug eluting coating may comprise drugs/compounds now known or later developed that inhibit neointimal growth.

It is contemplated that both the endothelial coating 820 and the drug eluting coating 824 may be applied to a graft. Typically, in such embodiments, the endothelial coating 820 will be applied on top of or over the drug eluting coating 824, though in some embodiments, the drug eluting coating may be on top of the endothelial coating. The endothelial coating 820 may be such that compounds of the drug eluting coating 824 may pass through the endothelial coating to prevent cellular proliferation.

Figure 8C:
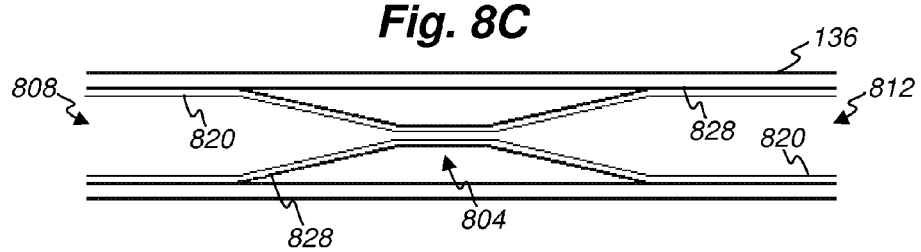
FIGS. 8C-8F are cross section views illustrating various exemplary improved vascular grafts.
Figure 8E:
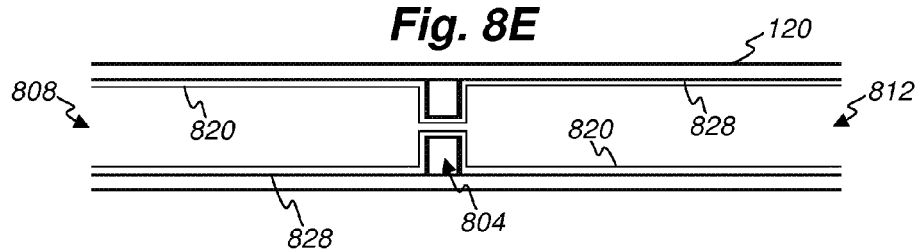
Figure 8D:
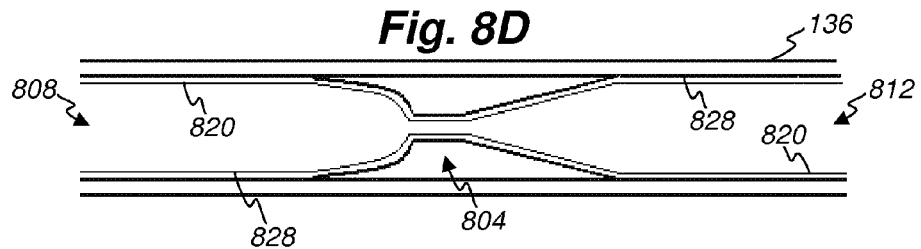
Figure 8F:
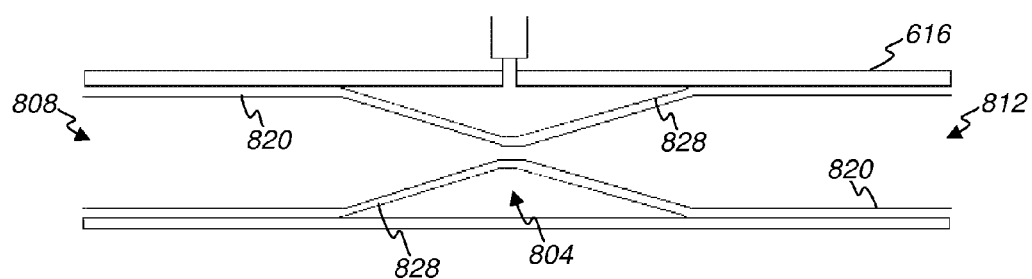

FIGS. 8C-8F illustrate various graft configurations that may include an endothelial coating 820, drug eluting coating 824, or both. It is noted that though particular grafts have been illustrated, the improved dialysis graft may have other configurations as well. FIGS. 8C-8D illustrate an endothelial coating 820 or drug eluting coating 824 as may be applied to a SAVE graft 136. As can be seen, the endothelial coating 820 or drug eluting coating 824 lines the fluid pathway of the SAVE graft 136 to prevent clotting and prevent cellular proliferation thus improving graft patency. FIG. 8E illustrates another graft configuration improved by an endothelial coating 820 or drug eluting coating 824. The endothelial coating 820 or drug eluting coating 824 (or both), may also be used with grafts having an adjustable stenosis, such as the AVG 120 of FIG. 8F which has a balloon adjustable central stenosis 804.

Figure 8G:
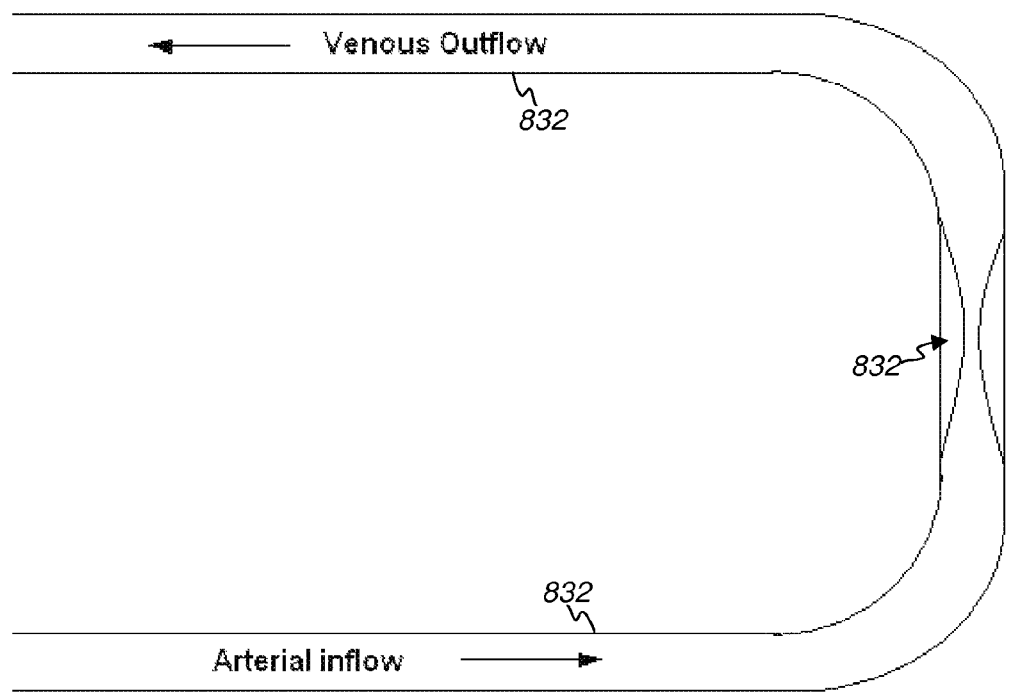
FIG. 8G is a cross section view illustrating an exemplary improved vascular graft in place.

FIG. 8G illustrates an example environment of use for the endothelial coating or drug eluting coating. For example, the endothelial coating or drug eluting coating may line the central stenosis 804 and/or other portions of the lumen 832 providing blood flow to and from the central stenosis.

Figure 9A:
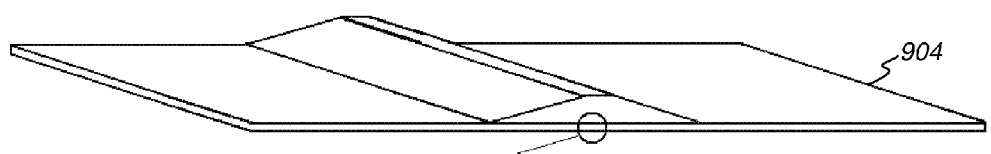
FIGS. 9A-9C illustrate formation of an exemplary improved vascular graft.
Figure 9B:
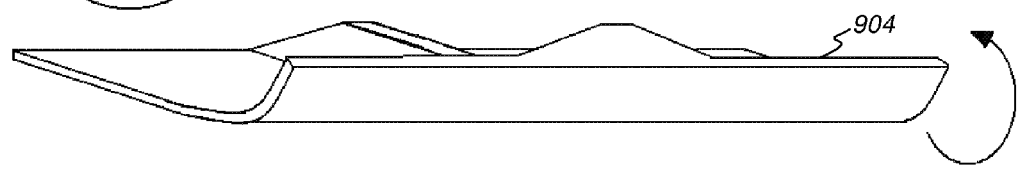
Figure 9C:
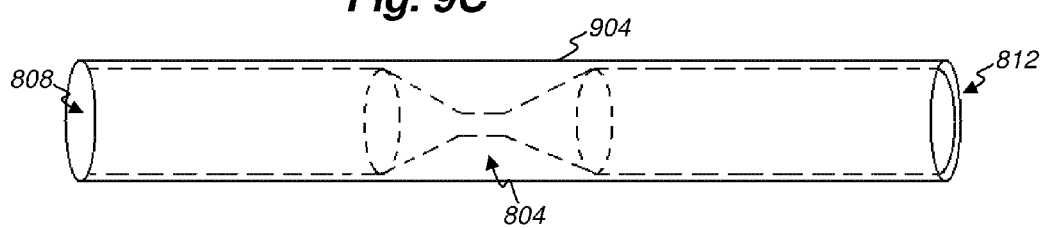

Formation of an improved dialysis graft will now be described with regard to FIGS. 9A-9C. FIG. 9A illustrates a sheet 904 of endothelial material, such as endothelial cells. As can be seen, the sheet 904 may comprise a form or shape, which may be manipulated to form a tubular graft having a stenosis. For example, in FIG. 9B, the sheet 904 is being rolled. The ends of the sheet 904 may then be attached or connected to form the exemplary AVG 120 of FIG. 9C having a central stenosis 804. A variety of graft designs may be formed in this way. It is noted that sheet 904 need not have a protrusion used to form the stenosis 804. Instead, the sheet 904 may be planar such as to form a graft without a stenosis.

It is contemplated that the endothelial material may itself be formed to create a graft with or without a central or other stenosis. Alternatively, the endothelial material may be applied to a substrate having a form or shape that may be manipulated to form a graft with or without a central or other stenosis. For example, the sheet 904 of FIG. 9A may comprise both a substrate which forms the structure of the sheet and a coating or lining of endothelial material that is applied to the substrate.

As will be described in the following, a stenosis may be created within a preexisting graft or fistula by an endovascular stent using a percutaneous technique. Stents are commonly used to expand and help keep vessels open to maintain patency. As will be described, a expanding stent may be lined, coated, or covered with an endothelial coating, drug eluting coating, or both. In this manner the benefits of the endothelial coating, drug eluting coating, or both may be applied to the stent.

Figure 10:
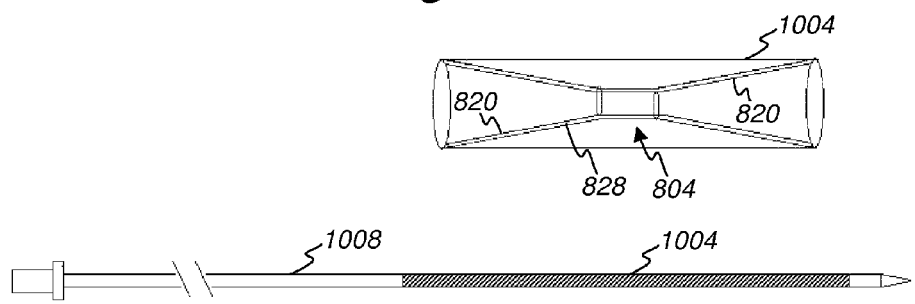
FIG. 10 is a cross section view illustrating an exemplary improved vascular graft and deployment sheath.

FIG. 10 illustrates an improved stent 1004 in an expanded state and the improved stent in a collapsed state for deployment by a deployment sheath 1008. A drug eluting coating, endothelial coating, or both may line or cover the interior surface of the stent 1004. As can be seen, the stent may collapse and be stored within the deployment sheath 1008 for placement within the vascular system. The drug eluting or endothelial coating may be resilient or flexible to allow the stent to collapse and expand without damaging the coatings.

Figure 11A:
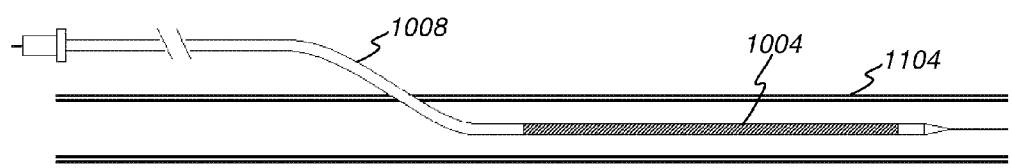
FIGS. 11A-11D illustrate deployment of an exemplary improved vascular graft within a vessel.

Implantation of the improved stent 1004 will now be described with regard to FIGS. 11A-11D. As shown in FIG. 11A, the deployment sheath 1008 may be advanced into a lumen 1104, which may be a lumen of a patient's vascular system including any preexisting grafts implanted into the patient. It is noted that a wire 1108 may first be advanced into the lumen 1104 such as to guide the deployment sheath 1008. For example, the deployment sheath 1008 in one embodiment, may be advanced to a desired position within a lumen 1104 by advancing the sheath over a previously inserted wire 1108. As can be seen in FIG. 11A, the deployment sheath 1008 has been advanced to a central location within the lumen 1104 to deploy the stent 1004.

Figure 11B:
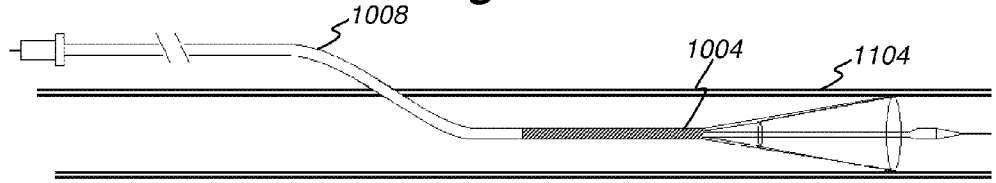
Figure 11C:
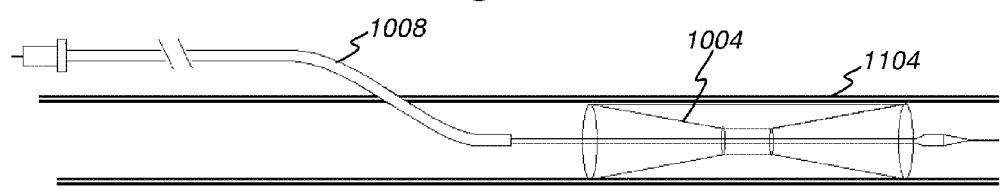
Figure 11D:
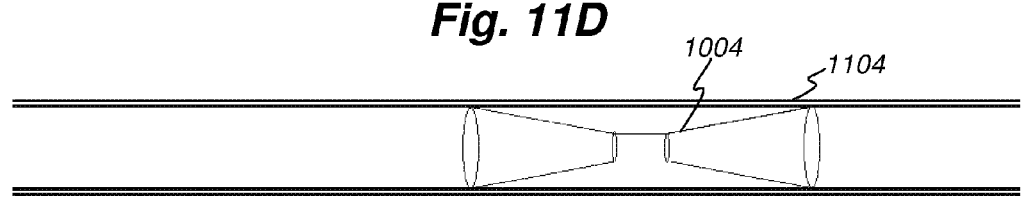

The deployment sheath 1008 may then be retracted or removed to deploy the stent 1004, such as shown in FIGS. 11B-11C. As can be seen, the stent 1004 may automatically expand as it is deployed or released from the deployment sheath 1008. FIG. 11B illustrates the stent 1004 partially deployed while FIG. 11C illustrates the stent fully deployed and expanded. As can be seen, the stent 1004 forms a seal around the interior surface of the lumen 1104. In this manner blood flow through the lumen 1104 travels through the stent 1004. Because the stent 1004 is lined with one or more drug eluting coatings, endothelial coatings, or both, blood flow through the stent improved along with patency. Moreover, the stent 1004 provides the desired stenosis (as shown by the narrowed portion of the stent) while providing such improved flow and patency. As shown in FIG. 11D, the deployment sheath 1008 and wire 1108 may be withdrawn from the lumen 1104 to complete the implantation procedure.

An apparatus and method for using a segment of a patient's vascular system (typically a vein) for use as a lining of a stenosis is also disclosed herein. Because a patient's vein possesses an endothelium, the lined stenosis will automatically be given the properties needed to maintain patency. As will be further described below, a segment of a patient's vein or other vessel may be harvested and used to form a stenosis using an endothelial scaffold. In addition, a rolled endothelial sheet, such as described above with regard to FIGS. 9A-9C may be used with the endothelial scaffold. As used herein, the term endothelial lumen refers to a conduit, channel, lumen, vessel, tubular structure, or the like having an endothelial lining. Such term includes the rolled endothelial sheet discussed above and natural vessels harvested from a person.

Figure 12:
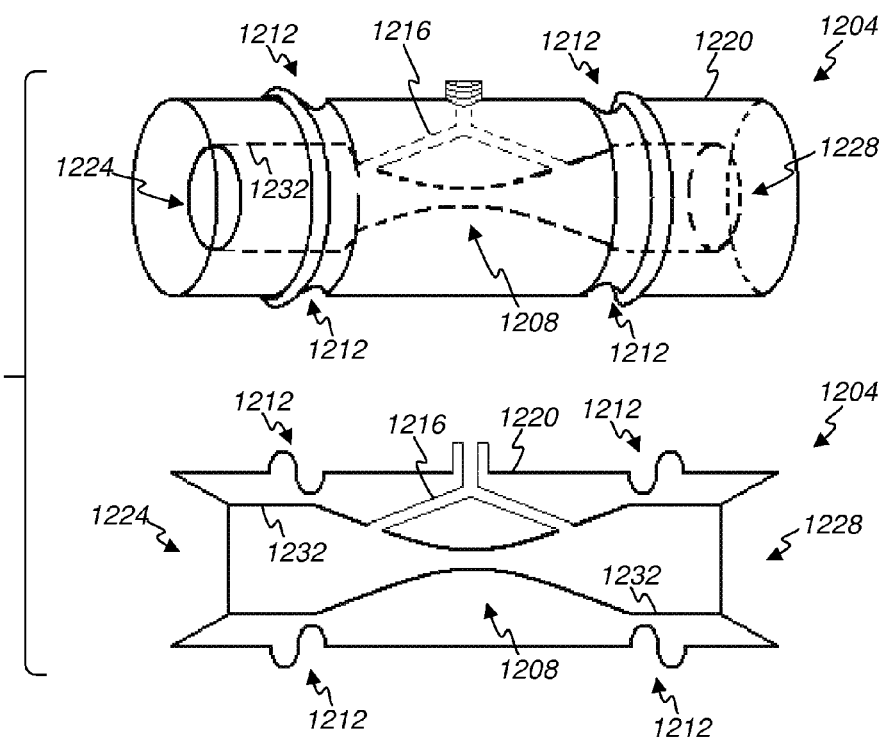
FIG. 12 is a perspective and side cross section view of an exemplary endothelial scaffold.

FIG. 12 illustrates an exemplary endothelial scaffold 1204 in a perspective view and a cross section view. Though the following is described with regard to a vein, it is contemplated that other endothelial lumen may be used in lieu of a vein. In general the endothelial scaffold 1204 provides support to a harvested vein allowing such vein to form a stenosis. The endothelium of the endothelial scaffold 1204 will typically line an interior portion of the scaffold to improve blood flow and reduce clotting. In this manner, the benefits of the vein's endothelial cells may be applied to blood flowing through the stenosis created by the vein and endothelial scaffold 1204.

The endothelial scaffold 1204 may comprise a body 1220 having a tubular configuration. In one or more embodiments, the body 1220 may have a channel 1232 or opening which extends from a first end 1224 to a second end 1228 of the body. This channel 1232 will typically be configured to receive a portion of a vein, as will be described further below. The channel 1232 may comprise a tapering or narrowing shape. For instance, in FIG. 12 the channel 1232 has a narrowed section 1208 configured to provide a stenosis. It is contemplated that the narrowed section 1208 may be centrally located along the channel 1232, such as shown, or may be positioned at the distal or proximal ends of the opening. The narrowed section 1208 illustrated utilizes a curved shape. It is contemplated that the narrowed section 1208 may be various shapes so long as the narrowing is achieved. For example, the narrowed section 1208 may have a shape the same as or similar to those illustrated in FIGS. 8C-8F. The narrowed section 1208 may be formed by a protrusion extending inward from the surface of the channel in one or more embodiments. For example, a curved protrusion may extend radially inward, such as to form the narrowed section 1208 of FIG. 12.

In one or more embodiments, the openings at the first and/or second ends 1224,1228 of the body 1220 may taper inward, such as illustrated in FIG. 12. The tapered openings may reduce the width of the body at the openings (at the first and/or second ends 1224,1228), such as to allow a vein to be more easily rolled over the body as will be described further below.

It is contemplated that the surface of the channel 1232 may be coated with one or more drug eluting coatings, such as described. In combination with the endothelium of the vein, such coatings help further increase graft patency further.

Figure 13A:
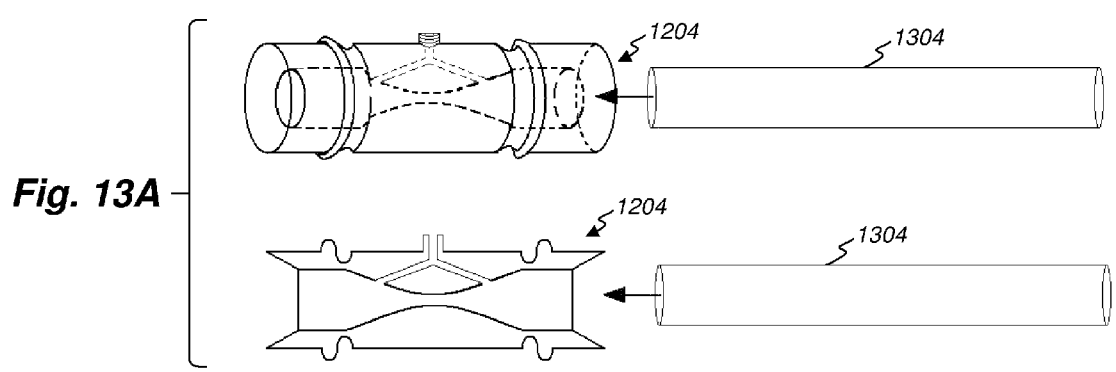
FIGS. 13A-13H illustrate harvesting of a natural vessel with an exemplary endothelial scaffold.
Figure 13B:
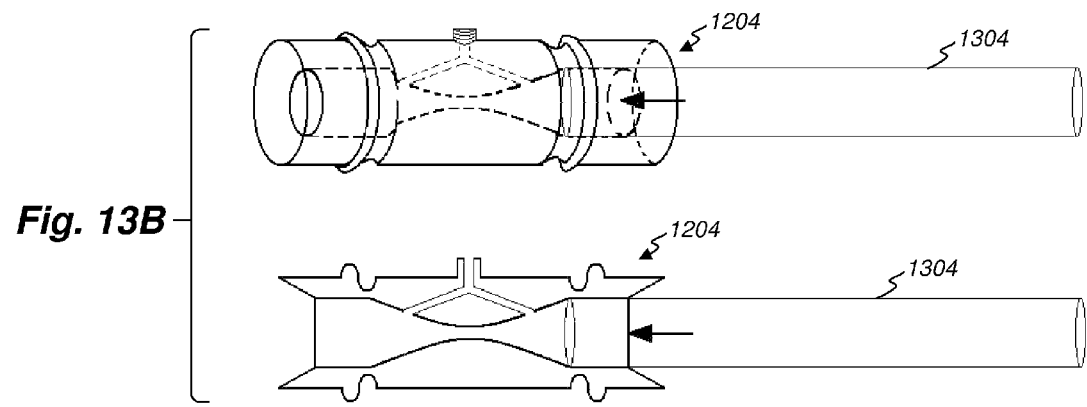
Figure 13C:
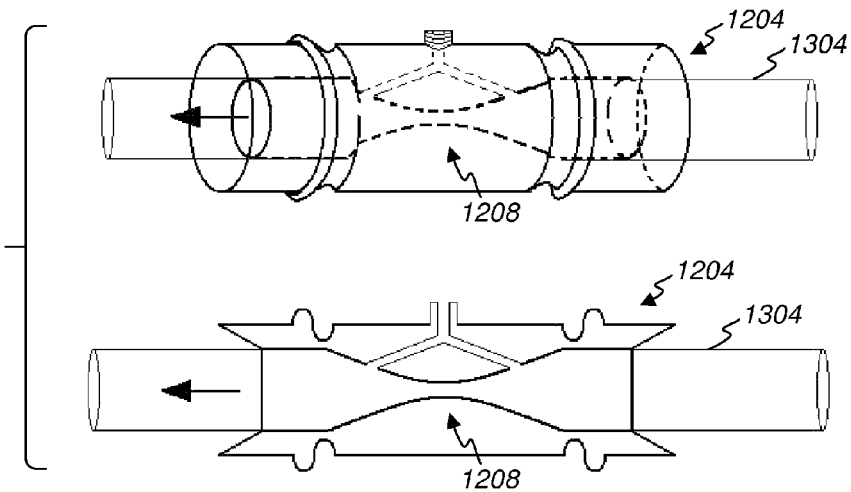

Operation of the endothelial scaffold will now be described with regard to FIGS. 13A-13L. FIG. 13A illustrates a vein 1304 adjacent the endothelial scaffold 1204. As indicated by the leftward pointing arrows, the vein 1304 may be inserted into the channel 1232 of the endothelial scaffold 1204. FIG. 13B illustrates a vein 1304 partially inserted into the endothelial scaffold 1204. FIG. 13C illustrates the vein 1304 inserted into the endothelial scaffold 1204 and extending outward from the endothelial scaffold. As can be seen, the vein 1304 (being a flexible structure) takes the shape of the narrowed section 1208 of the endothelial scaffold 1204. Accordingly, a stenosis is formed within the vein 1304. As can also be seen, the vein 1304 now lines the interior surface of the endothelial scaffold' channel 1232. In this manner, the endothelium of the vein 1304 contacts blood flowing through the endothelial scaffold 1204, reducing the risk of clotting and improving blood flow.

Figure 13D:
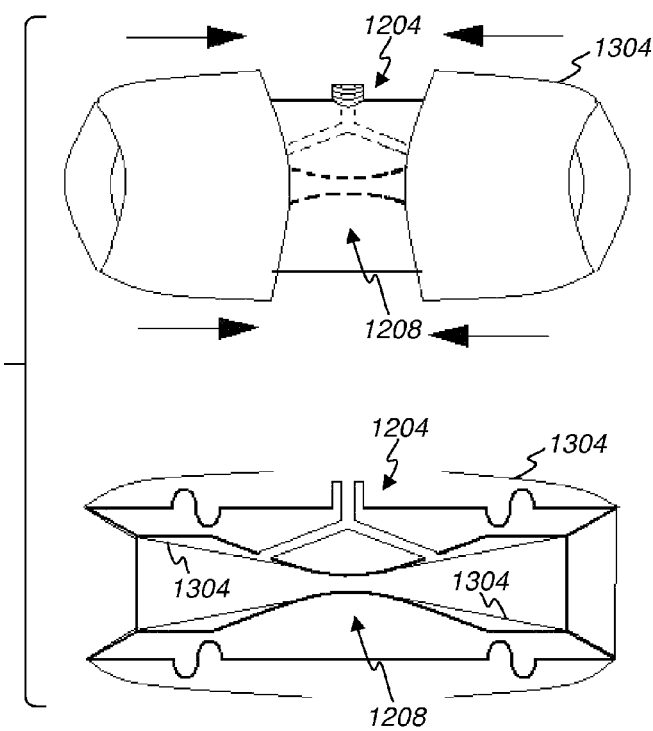

The length of the vein 1304 may be cut or set such that a portion of the vein extends outward from the first end 1224 and second end 1228 of the endothelial scaffold 1204. An example of this is shown in FIG. 13C. The ends of the vein 1304 may then be rolled over the exterior of the endothelial scaffold 1204, such as shown in FIG. 13D, to secure the vein 1304 to the endothelial scaffold 1204.

Referring back to FIG. 12, the endothelial scaffold 1204 may comprise one or more fixation elements 1212 which may be used to secure the vein 1304 to the endothelial scaffold 1204. In one or more embodiments, a fixation element 1212 may be configured to hold a portion of the vein 1304 in place. In FIG. 12 for example, the fixation elements 1212 comprise a groove on the exterior surface of the endothelial scaffold 1204. The groove may be configured to accept a portion of the vein 1304 as well as a fixation band which secures the portion of the vein 1304 within the groove.

Figure 13E:
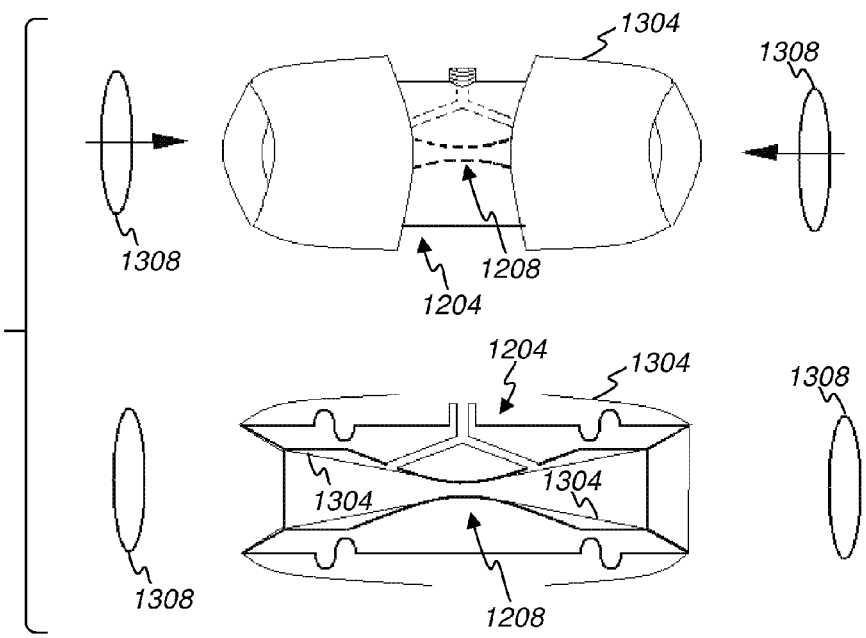
Figure 13F:
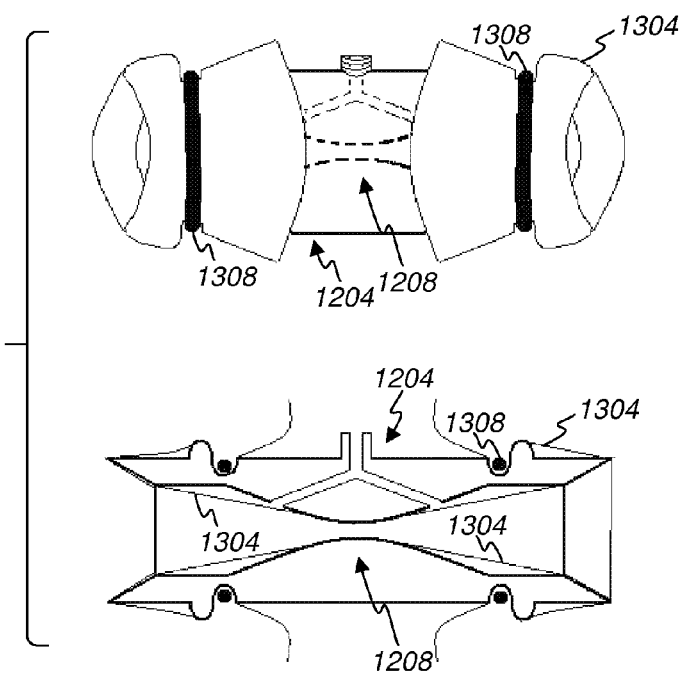

FIGS. 13E-13F illustrate the process by which one or more fixation bands 1308 may be used to secure a vein 1304. As can be seen in FIG. 13F, the fixation bands 1308 may be placed over the rolled ends of the vein 1304 such that the fixation bands are positioned within the fixation elements 1212. In this manner, the fixation bands 1308 hold the vein 1304 in position at the fixation elements 1212. Typically, at least one fixation band 1308 and fixation element 1212 will be used at both ends of the vein 1304 to secure both ends of the vein to the endothelial scaffold 1204.

The fixation bands 1308 may have various configurations. For example, a fixation band 1308 may be elastic, flexible, resilient and/or stretchable in one or more embodiments. This permits the fixation band 1308 to stretch or expand to be fitted over the vein 1304 and endothelial scaffold 1204 and then contract to secure the vein in position relative to the endothelial scaffold. In other embodiments, the fixation bands 1308 may be an elongated structure which is fitted and/or tightened around the vein 1304 and endothelial scaffold 1204 to secure the vein 1304 in position. The ends of fixation bands 1308 of such embodiments may be attached or secured to one another to form a loop around the vein 1304 and endothelial scaffold 1204.

In addition to a groove or inset portion, it is contemplated that in some embodiments the fixation elements 1212 may comprise a protruding portion, such as can be seen in FIG. 13F. The protruding portion may be adjacent the inset portion. In addition, the protruding portion may be closer to the end of the endothelial scaffold 1204 than the inset portion. This is beneficial in that it allows a fixation element 1212 to better secure the vein 1304. To illustrate, as shown in FIG. 13F, the vein 1304 bends over the protruding portion and into the inset portion of the fixation elements 1212. This increases the amount of force necessary to pull the vein 1304 out of the inset portion. It is noted that the protruding portion may not be provided where the inset portion is deemed sufficient to secure the vein 1304.

Figure 13G:
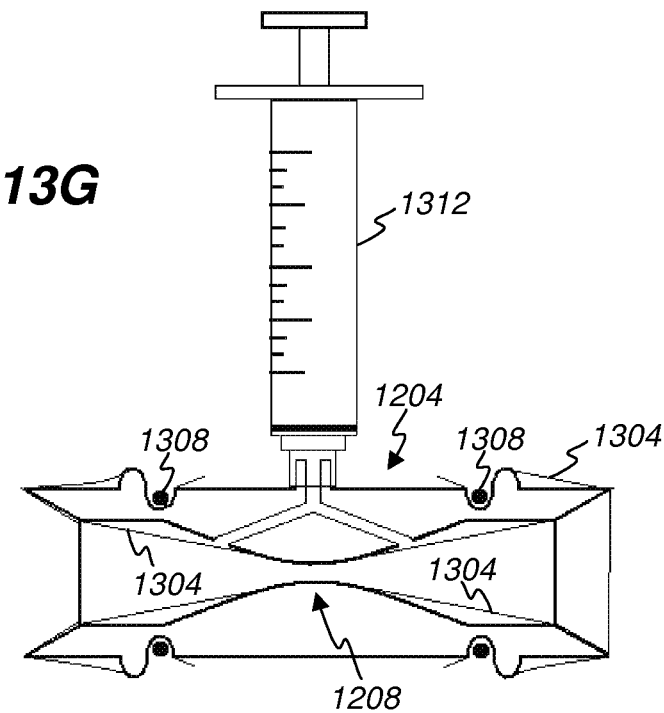
Figure 13H:
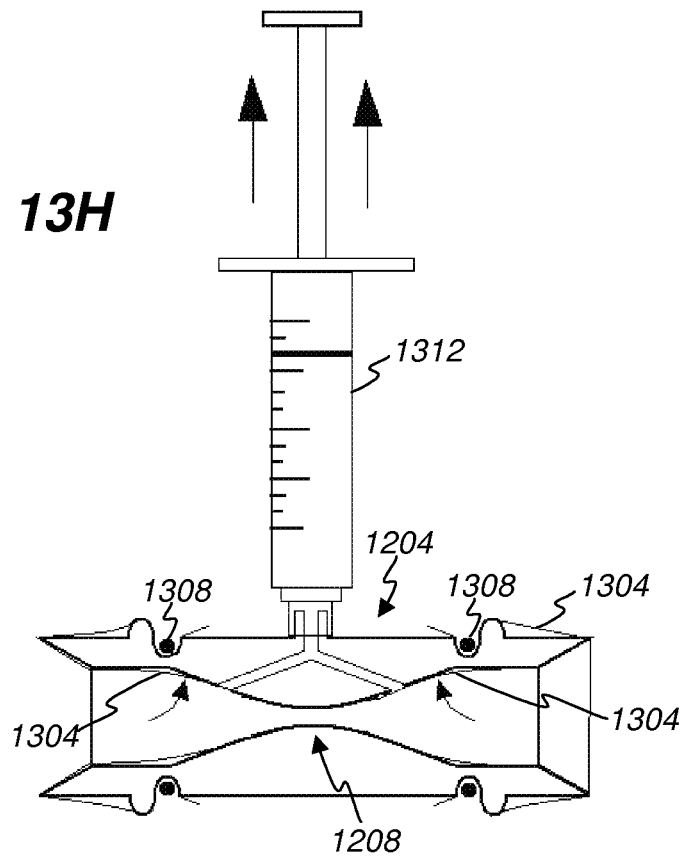

It can be seen in FIGS. 13G-13H that excess portions of the vein 1304 may be trimmed away if desired, once the vein 1304 has been secured. In addition, it can be seen that one or more gaps between the vein 1304 and interior surface of the channel 1232 may exist, especially after the ends of the vein 1304 have been rolled over the endothelial scaffold 1204, pulled tight, and secured in position with one or more fixation bands 1308. The gaps may be eliminated by withdrawing air from the gaps to thereby pull the vein 1304 to the interior surface of the channel 1232.

Referring back to FIG. 12, the endothelial scaffold 1204 may optionally include one or more conduits 1216 to properly seat the vein once it is in the opening 1232. In general, these conduits 1216 may be configured to allow air to be removed from any gaps between the vein 1304 and the interior surface of the channel 1232.

The conduits 1216 may extend to the inner surface of the channel 1232 and be accessible from the exterior of the endothelial scaffold 1204. As can be seen, the conduits 1216 may connect to one another or branch from one or more other conduits. The conduits 1216 may also extend to various areas of the interior surface of the channel 1232. This is beneficial in that it allows gaps to be eliminated regardless of their location. Typically, the conduits 1216 will extend to areas where a gap is likely. For instance, in FIG. 13G, the conduits 1216 extend to the angled portion of the narrowed section 1208 as there is likely to be a cap there if the vein 1304 is pulled tight as it is being secured to the endothelial scaffold 1204.

FIG. 13G also illustrates external access to the conduits 1216 by a gas removal device 1312. As shown, the gas removal device 1312 is a syringe that has been coupled with the conduits 1216. It is contemplated that various other mechanisms may be coupled to the conduits 1216 to withdraw air. As can be seen in FIG. 13H, as air is withdrawn from the endothelial scaffold 1204, the gaps between the vein 1304 and channel 1232 of the endothelial scaffold are reduced or eliminated. This is beneficial in that it causes the vein 1304 to take the shape of the channel 1232. A one-way valve, cap, cover or the like may be used to prevent air from returning into the endothelial scaffold 1204 once withdrawn.

Figure 14A:
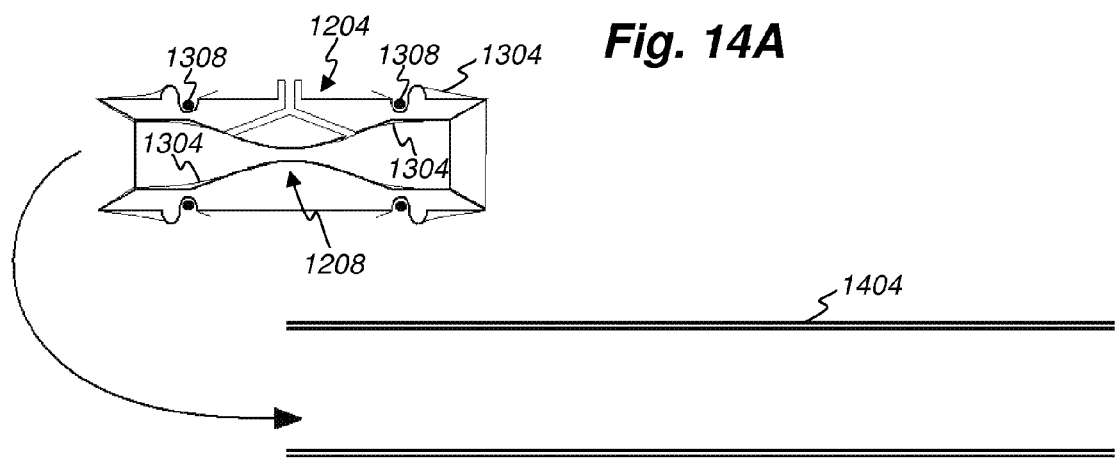
FIGS. 14A-14C illustrate implantation of an exemplary improved vascular graft comprising an endothelial scaffold.
Figure 14B:
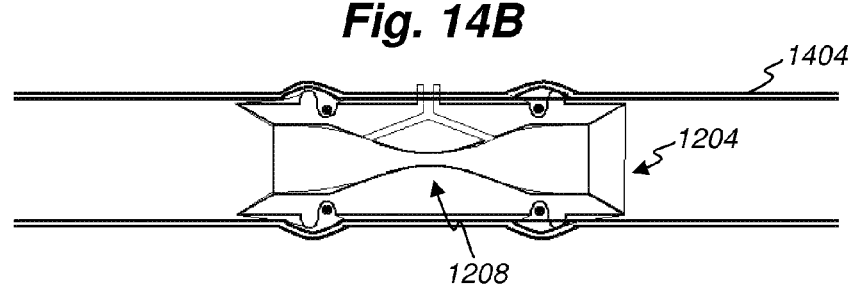
Figure 14C:
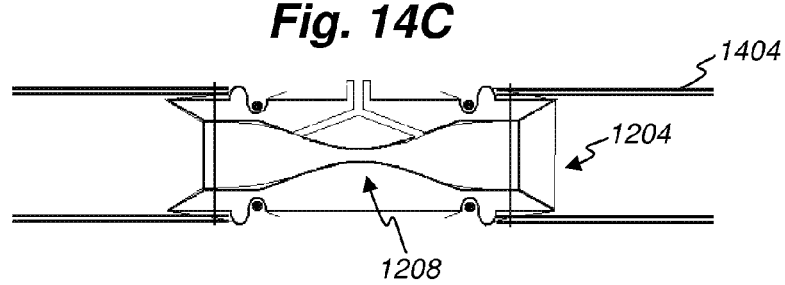

The endothelial scaffold 1204 may then be implanted in the patient. It is contemplated that the endothelial scaffold 1304 may be implanted in a manner similar to those used to implant traditional grafts. FIGS. 14A-14C illustrate exemplary ways in which the endothelial scaffold 1204 may be implanted. As shown by FIGS. 14A-14B, the endothelial scaffold 1204 may be implanted by inserting it into a graft 1404. Alternatively, the endothelial scaffold 1204 may be implanted by attaching its ends to those of one or more grafts 1404 such as shown in FIG. 14C. Attachment may occur by a circumferential suture or an integrated technique in one or more embodiments. As can be seen, the endothelial scaffold 1204 and harvested vein 1304 provide a stenosis lined with the endothelium of the vein. Blood flowing through the stenosis is thus improved along with the patency of any associated graft or implant of a patient's vascular system.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A graft comprising:
   a scaffold having a first end and a second end, the scaffold configured to form a channel to accept an endothelial lumen, the channel comprising a first opening at the first end and a second opening at the second end;
   an endothelial lumen in the channel;
   one or more conduits extending from an exterior surface of the scaffold to an inner surface of the channel;
   a valve in fluid communication with the one or more conduits, the valve configured to prevent gas from entering the one or more conduits while permitting gas to be withdrawn from the one or more conduits; and
   a protrusion extending from an inner surface of the channel, the protrusion configured to narrow a portion of the channel to provide a stenosis in the channel.

2. The graft of claim 1 wherein the endothelial lumen comprises a sheet of endothelial material, the sheet of endothelial material being formed into a lumen through which blood may flow.

3. The graft of claim 1 further comprising a drug eluting material on an interior surface of the endothelial lumen, the drug eluting material configured to release one or more cellular growth inhibitors.

4. The graft of claim 1 further comprising one or more grooves on the exterior surface of the scaffold, the one or more grooves configured to engage one or more fixation bands to secure the endothelial lumen in place.

5. The graft of claim 4 further comprising one or more protruding portions on the exterior surface of the scaffold, the one or more protruding portions located adjacent the one or more grooves.

6. The graft of claim 1, wherein the scaffold has a reduced thickness at the first end configured to allow the endothelial lumen to be rolled over the scaffold at the first end.

7. The graft of claim 1, wherein the one or more conduits extend to a location on the interior surface of the channel that is adjacent the protrusion.

8. A graft comprising:
   a scaffold having a first end and a second end, the scaffold configured to form a channel to accept an endothelial lumen, the channel comprising a first opening at the first end and a second opening at the second end;
   an endothelial lumen in the channel;
   one or more conduits extending from an exterior surface of the scaffold to an inner surface of the channel;
   a cover at the exterior surface of at least one of the one or more conduits, the cover configured to prevent gas from entering the one or more conduits while permitting gas to be withdrawn from the one or more conduits; and
   a protrusion extending from an inner surface of the channel, the protrusion configured to narrow a portion of the channel to provide a stenosis in the channel.

9. The graft of claim 8 wherein the endothelial lumen comprises a sheet of endothelial material, the sheet of endothelial material being formed into a lumen through which blood may flow.

10. The graft of claim 8 further comprising a drug eluting material on an interior surface of the endothelial lumen, the drug eluting material configured to release one or more cellular growth inhibitors.

11. The graft of claim 8 further comprising one or more grooves on the exterior surface of the scaffold, the one or more grooves configured to engage one or more fixation bands to secure the endothelial lumen in place.

12. The graft of claim 11 further comprising one or more protruding portions on the exterior surface of the scaffold, the one or more protruding portions located adjacent the one or more grooves.

13. The graft of claim 8 wherein the scaffold has a reduced thickness at the first end configured to allow the endothelial lumen to be rolled over the scaffold at the first end.

14. The graft of claim 8 wherein the one or more conduits extend to a location on the interior surface of the channel that is adjacent the protrusion.

* * * * *